US012703741B2

(12) United States Patent
Gyuris et al.

(10) Patent No.: US 12,703,741 B2
(45) Date of Patent: Aug. 11, 2026

(54) TREATMENT OF CONGESTIVE HEART FAILURE AND OTHER CARDIAC DYSFUNCTION USING A GDF15 MODULATOR

(71) Applicant: AVEO Pharmaceuticals, Inc., Boston, MA (US)

(72) Inventors: Jeno Gyuris, Lincoln, MA (US); Lorena Lerner, Newton Centre, MA (US)

(73) Assignee: AVEO Pharmaceuticals, Inc., Boston, MA (US)

( * ) Notice: Subject to any disclaimer, the term of this patent is extended or adjusted under 35 U.S.C. 154(b) by 127 days.

(21) Appl. No.: 17/649,732

(22) Filed: Feb. 2, 2022

(65) Prior Publication Data

US 2022/0403015 A1 Dec. 22, 2022

Related U.S. Application Data

(63) Continuation of application No. 16/177,792, filed on Nov. 1, 2018, now abandoned, which is a continuation of application No. 15/320,094, filed as application No. PCT/US2015/036790 on Jun. 19, 2015, now abandoned.

(60) Provisional application No. 62/015,093, filed on Jun. 20, 2014.

(51) Int. Cl.
*C07K 16/22* (2006.01)
*A61K 39/00* (2006.01)

(52) U.S. Cl.
CPC ........ *C07K 16/22* (2013.01); *A61K 2039/505* (2013.01); *C07K 2317/24* (2013.01); *C07K 2317/56* (2013.01); *C07K 2317/565* (2013.01); *C07K 2317/76* (2013.01)

(58) Field of Classification Search
CPC ....... C07K 16/22; A61K 39/395; C12N 15/13
See application file for complete search history.

(56) References Cited

U.S. PATENT DOCUMENTS 5,994,102 A 11/1999 Hudson et al.
6,051,424 A 4/2000 Kato et al.
6,180,602 B1 1/2001 Kato et al.
6,420,543 B1 7/2002 Lee et al.
6,465,181 B2 10/2002 Billing-Medel et al.
6,500,638 B2 12/2002 Hudson et al.
6,521,227 B1 2/2003 Hudson et al.
7,157,235 B2 1/2007 Breit et al.
7,282,351 B2 10/2007 Hudson et al.
7,514,221 B2 4/2009 Breit et al.
7,741,055 B2 6/2010 Hudson et al.
7,919,084 B2 * 4/2011 Breit ...................... C07K 16/22 514/1.9
7,968,303 B2 6/2011 Breit et al.
8,173,434 B2 5/2012 Fan et al.
8,192,735 B2 6/2012 Breit et al.
9,175,076 B2 11/2015 Lerner et al.
9,334,331 B2 * 5/2016 Igawa ...................... A61P 7/00
9,725,505 B2 * 8/2017 Lerner ...................... A61P 3/02
10,421,807 B2 * 9/2019 Gonzales ................ A61P 11/00
10,597,444 B2 3/2020 Lerner et al.
2003/0232385 A1 12/2003 Breit et al.
2006/0263774 A1 11/2006 Clark et al.
2007/0207462 A1 9/2007 Ichinose et al.
2009/0004181 A1 * 1/2009 Breit ...................... C07K 16/24 435/14
2009/0021293 A1 1/2009 Hebert et al.
2010/0266707 A1 * 10/2010 Breit ...................... A61P 31/06 424/529
2011/0033886 A1 2/2011 Hess et al.
2011/0065204 A1 3/2011 Wollert et al.
2011/0262444 A1 10/2011 Kim
2011/0300548 A1 12/2011 Lambrecht et al.
2012/0083420 A1 4/2012 Clark et al.
2014/0193427 A1 7/2014 Lerner et al.

FOREIGN PATENT DOCUMENTS

CA 2534871 A1 8/2007
EP 1884777 A1 2/2008
EP 2047275 A2 4/2009
EP 2103943 A1 9/2009
WO WO-1994003599 A1 2/1994
WO WO-1996018730 A1 6/1996
WO WO-1997000958 A1 1/1997
WO WO-1999006445 A1 2/1999
WO WO-2000020449 A2 4/2000
WO WO-2000056352 A2 9/2000
WO WO-2000070051 A1 11/2000

(Continued)

OTHER PUBLICATIONS

Feldman, 2002, Molecular Pharmacology. 61(4): 707-709.*
Janigro (2008, Epilepsy Currents 8(1): 23-24).*
Kempf et al. (2007, Clin. Chem. 53:284-291).*
Kempf et al. (2006, Cir. Res. 98:351-360).*
Xu et al. (2006, Circ. Res. 98:342-350).*
Tobin et al. (2006, Drug Discovery Today 11:405-411).*
Lajer et al. (2010, Diabetes Care 33:1567-1572).*
Al Qaraghuli et al. (2020, Nature Scientific Reports 10:13969).*
Edwards et al. (2003, JMB 334:103-118).*
Lloyd et al. (2009, Protein Engineering, Eng. Design & Selection 22(3): 159-168).*

(Continued)

*Primary Examiner* — Vanessa L. Ford
(74) *Attorney, Agent, or Firm* — Morgan, Lewis & Bockius LLP

(57) ABSTRACT

The invention provides methods and compositions of treating a subject having a cardiac-related disorder such as congestive or chronic heart failure (CHF), cardiac hypertrophy, cardiac hypotrophy, and other cardiac myopathies/dystrophies. The methods comprise administering an effective amount of a composition that modulates, for example, reduces or inhibits, GDF15 activity in the subject.

6 Claims, 8 Drawing Sheets

Specification includes a Sequence Listing.

(56) References Cited

FOREIGN PATENT DOCUMENTS

| | | | |
|---|---|---|---|
| WO | WO-2002020759 | A2 | 3/2002 |
| WO | WO-2004043385 | A2 | 5/2004 |
| WO | WO-2005044990 | A2 | 5/2005 |
| WO | WO-2005/099746 | A1 | 10/2005 |
| WO | WO-2008015254 | A2 | 2/2008 |
| WO | WO-2009/021293 | A1 | 2/2009 |
| WO | WO-2009/046495 | A1 | 4/2009 |
| WO | WO-2011117254 | A1 | 9/2011 |
| WO | WO-2012113103 | A1 | 8/2012 |
| WO | WO-2014/100689 | A1 | 6/2014 |

OTHER PUBLICATIONS

Goel et al. (2004, J. Immunol. 173: 7358-7367).*
Khan et al. (2014, J. Immunol. 192: 5398-5405).*
Poosarla et al. (2017, Biotechn. Bioeng. 114(6): 1331-1342).*
Rabia, et al. (2018, Biochemical Engineering Journal 137:365-374).*
Christensen et al., 2013, Endocrine 43:626-634.*
Klapholz et al. (2004, J. Am. Coll. Cardiol. 43(8):1432-1438).*
Gradman et al. (2006, Progress in Cardiovascular Disease 48(5):326-341).*
Montoro-Garcia et al. (2012, Eur. J. Internal Med. 23:169-174).*
Karavidas et al. (2010, Hellenic J. Cardiol. 51:421-427).*
Belluardo et al. (2006, Am. J. Physiol. Heart Circ. Physiol. 291:H1529-H1535).*
Eggers et al. (2008, Eur. Heart J. 29:2252-2258).*
Zhang et al. (2016, PLoS One 11(6):e0157372; doi:10.1371/journal.pone.0157372; pp. 1-16).*
Allan et al., "A selective androgen receptor modulator that reduces prostate tumor size and prevents orchidectomy-induced bone loss in rats." J Steroid Biochem Mol Biol. Jan. 2007;103(1):76-83.
Argiles et al., "Anti-inflammatory therapies in cancer cachexia." Eur J Pharmacol. Sep. 2011;668 Suppl 1:S81-6.
Baev et al., "Cardiac hypotrophy in young women with low blood pressure," Biology and Medicine 2014;6(1):1-6.
Bauerlein et al., "Efficacy of REGN1033, a fully human anti-myostatin antagonist antibody, in rodent muscle function." J. Cachexia Sarcopenia Muscle 2013;4:295-343 Abstract 4-06 from 7th Cachexia Conference, Kobe/Osaka, Japan, Dec. 9-11, 2013.
Baumgartner et al., "Epidemiology of sarcopenia among the elderly in New Mexico." Am J Epidemiol. Apr. 15, 1998;147(8):755-63.
Bauskin et al., "Role of macrophage inhibitory cytokine-1 in tumorigenesis and diagnosis of cancer." Cancer Res. May 15, 2006;66(10):4983-6.
Bialek et al., "A myostatin and activin decoy receptor enhances bone formation in mice." Bone. Mar. 2014; 60:162-171.
Bonaca MP et al., (2011), 'Growth Differentiation Factor-15 and Risk of Recurrent Events in Patients Stabilized After Acute Coronary Syndrome: Observations from Prove It-TIMI 22,' Anterioscler Thromb Vasc Biol, 31(1):203-10.
Bovee et al., "SERMs and SARMs: detection of their activities with yeast based bioassays." J. Steroid Biochem. Mol. Biol. 2010;118:85-92.
Breit et al. "The TGF-13 superfamily cytokine, MIC-1/GDF15: a pleotrophic cytokine with roles in inflammation, cancer and metabolism" Growth Factors. Oct. 2011;29(5):187-95.
Brown DA et al., (2002), 'Concentration in Plasma of Macrophage Inhibitory Cytokine-1 and Risk of Cardiovascular Events in Women: A Nested Case-Control Study,' Lancet, 359(9324):2159-63.
Cattadori G et al., (2011), 'Hemodynamic Effects of Exercise Training in Heart Failure,' J Card Fail, 17(11):916-22.
Chen et al., "Discovery and Therpeutic Promise of Selective Androgen Receptor Modulators." Mol. Interv. Jun. 2005; 5(3):173-188.
Clerico A et al., (2012), 'State of the Art of BNP and NT-proBNP Immunoassays: The CardioOrmoCheck Study,' Clin Chim Acta, 414:112-9.
Dalton et al., "The selective androgen receptor modulator GTx-024 (enobosarm) improves lean body mass and physical function in healthy elderly men and postmenopausal women: results of a double-blind, placebo-controlled phase II trial." J Cachexia Sarcopenia Muscle. Sep. 2011;2(3):153-161.
Davenport and Wright, "Treating Obesity: is it all in the gut?" Drug Discov Today (2013), <http://dx.doi.orp/10.1016/j.drudis.2013.10.025>.
DeBoer and Marks, "Cachexia: lessons from melanocortin antagonism." Trends Endocrinol Metab. Jul. 2006;17(5):199-204.
DLibel S et al., 'Chapter 6: Antibody Affinity,' Handbook of Therapeutic Antibodies. (2nd Ed, 2010), S DLibel and JM Reichert (eds), Wiley-VCH Verlag GmbH, Weinheim, DE (Pub), pp. 119-144 XP007913671.
Enomoto et al., "Suppression of cancer cachexia by 205,21-epoxy-resibufogenin-3-acetate-a novel nonpeptide IL-6, receptor antagonist." Biochem Biophys Res Commun. Oct. 22, 2004;323(3):1096-102.
Evans et al., "Cachexia: a new definition." Clin Nutr. Dec. 2008;27(6):793-9.
Faggiano P et al., (1997), 'Assessment of Oxygen Uptake During the 6-Minute Walking Test in Patients with Heart Failure: Preliminary Experience with a Portable Device,' Am Heart J, 134(2 Pt 1):203-6.
Fairlie et al., "Expression of a TGF-beta superfamily protein, macrophage inhibitory cytokine-1, inthe yeast *Pichia pastoris.*" Gene. Aug. 22, 2000;254(1-2):67-76.
Fearon et al., "Cancer cachexia: mediators, signaling, and metabolic pathways." Cell Metab. Aug. 8, 2012;16(2):153-66.
Fearon et al., "Definition and classification of cancer cachexia: an international consensus." Lancet Oncol. May 2011;12(5):489-95.
Fong et al. "Cachectin/TNF or IL-1 alpha induces cachexia with redistribution of body proteins." Am J Physiol. Mar. 1989;256(3 Pt 2):R659-65.
Foote et al., (1992), "Antibody Framework residues affecting the conformation of the hypervariableloops," J. Mol. Biol., 224:487-499.
Galvani M et al., (1997), 'Prognostic Influence of Elevated Values of Cardia Troponin I in Patientswith Unstable Angina,' Circulation, 95(8):2053-9.
Glass, "Signaling pathways perturbing muscle mass." Curr Opin Clin Nutr Metab Care. May 2010;13(3):225-9.
Green DJ et al., (2001), 'A Comparison of the Shuttle and 6 Minute Walking Tests with Measured Peak Oxygen Consumption in Patients with Heart Failure,' J Sci Med Sport, 4(3):292-300.
Guillory et al., "Chapter 3: The Role of Ghrelin in Anorexia-Cachexia Syndromes." Vitamins and Hormones. 2013; 92:61-106.
Heringlake M et al., (2013), 'Growth Differentiation Factor 15: A Novel Risk Marker Adjunct to the EuroSCORE for Risk Stratification in Cardiac Surgery Patients,' J Am Col Cardiol, 61(6):672-81.
Hinoi et al. "Positive regulation of osteoclastic differentiation by growth differentiation factor 15 upregulated in osteocytic cells under hypoxia" J Bone Miner Res. Apr. 2012;27(4):938-49.
Hryniewicz et al., Partial reversal of cachexia by beta-adrenergic receptor blocker therapy in patients with chronic heart failure. J Card Fail. Dec. 2003;9(6):464-8.
International Search Report (Form ISA/210) for Intentional Application No. PCT/US2015/036790 mailed Nov. 30, 2015 (7 pages).
Johnen H et al., (2007), 'Tumor-Induced Anorexia and Weight Loss are Mediated by the TGF-13 Superfamily Cytokine MIC-1,' Nat Med, 13(11):1333-40.
Joppa et al., "Central infusion of the melanocortin receptor antagonist agouti-related peptide (AgRP(83-132)) prevents cachexia-related symptoms induced by radiation and colon-26 tumors in mice." Peptides. Mar. 2007;28(3):63:636-42.
Kalinkovich and Livshits, (2015), "Sarcopenia—The search for emerging biomarkers", Aging Research Reviews, 22:58-71.
Kalinkovich et al., "Sarcopenia—The search for emerging biomarkers." Ageing research reviews vol. 22 (2015): 58-71.
Kempf et al. "The transforming growth factor-beta superfamily member growth-differentiation factor-15 protects the heart from ischemia/reperfusion injury." Circulation research vol. 98,3 (2006): 351-60.

(56) References Cited

OTHER PUBLICATIONS

Kempf T et al., (2006), 'The Transforming Growth Factor-13 Superfamily Member Growth-Differentiation Factor-15 Protects the Heart from Ischemia/Reperfusion Injury,' Circ Res, 98(3):351-60.
Kempf T et al., (2007), 'Circulating Concentrations of Growth-Differentiation Factor 15 in Apparently Health Elderly Individuals and Patients with Chronic Heart Failure as Assessed by a New Immunoradiometric Sandwich Assay,' Clin Chem, 53(2):284-91.
Kempf T et al., (2007), 'Prognostic Utility of Growth Differentiation Factor-15 in Patients with Chronic Heart Failure,' J Am Coll Cardiol, 50(11):1054-60.
Kempf T et al., (2011), 'GDF-15 is an Indicator of Leukocyte Integrin Activation Required for Survival and Myocardial Infarction in Mice,' Nat Med, 17(5):581-8.
Lajer et al. "Plasma growth differentiation factor-15 independently predicts all-cause and cardiovascular mortality as well as deterioration of kidney function in type 1 diabetic patients with nephropathy," Diabetes Care vol. 33,7 (2010): 1567-72.
Lajer M et al., (2010), 'Plasma Growth Differentiation Factor-15 Independently Predicts All-Cause and Cardiovascular Mortality as well as Deterioration of Kidney Function in Type 1 Diabetic Patients with Nephropathy,' Diabetes Care, 33(7):1567-72.
Lanier GM et al., (2012), 'Simple Prediction Formula for Peak Oxygen Consumption in Patients with Chronic Heart Failure,' J Exerc Sci Fit, 10(1):23-7.
Latini R et al., (2007), 'Prognostic Value of Very Low Plasma Concentrations of Troponin Tin Patients with Stable Chronic Heart Failure,' Circulation, 116(11):1242-9.
Inui, "Cancer anorexia-cachexia syndrome: current issues in research and management." Cancer J Clin. Mar.-Apr. 2002;52(2):72-91.
Lokireddy et al., "Myostatin is a novel tumoral factor that induces cancer cachexia." Biochem J. Aug. 15, 2012;446(1):23-36.
Lonberg N, (2008), 'Fully Human Antibodies from Transgenic Mouse and Phage Display Platforms,' Curr Opin Immunol, 20(4):450-9.
Lord et al. (2010, J. Small Animal Practice 51:210-218).
Marino et al., "The therapeutic potential of blocking the activin signalling pathway." Cytokine Growth Factor Rev. Oct. 2013;24(5):477-84.
Matthys and Billiau, "Cytokines and cachexia." Nutrition. Sep. 1997;13(9):763-70.
Meczekalski B et al., (2013), 'Long-Term Consequences of Anorexia Nervosa,' Maturitas, 75(3):215-20.
Mohler et al., "Nonsteroidal Selective Androgen Receptor Modulators (SARMs): Dissociating the Anabolic and Androgenic Activities of the Androgen Receptor for Therapeutic Benfit." J. Med. Chem. 2008;52(12):3597-3617.
Morales FJ et al., (1999), 'A Shuttle Walk Test for Assessment of Functional Capacity in Chronic Heart Failure,' Am Heart J, 138(2 Pt 1):291-8.
Muscaritoli et al., Consensus definition of sarcopenia, cachexia and pre-cachexia: joint document elaborated by Special Interest Groups (SIG) 'cachexia-anorexia in chronic wasting diseases' and 'nutrition in geriatrics.' Clin Nutr. Apr. 2010;29(2):154-9.
Nagata et al., "Design and synthesis of tricyclic tetrahydroquinolines as a new series of nonsteroidal selective androgen receptor modulators (SARMs)." Bioorg. Med. Chem. Lett. 2011;21:1744-1747.
Ng et al., Synthesis of potent and tissue-selective androgen receptor modulators (SARMs): 2-(2,2,2)-Trifluoroethyl-benzimidazole scaffold. Bioorg Med Chem Lett. Mar. 15, 2007;17(6):1784-7.
Olson et al. (2007, J. Cardiac Failure 13(2):100-107).
Peterson, "Pressure Overload Hypertrophy and Congestive Heart Failure: Where is the 'Achilles' Heel?" J. Am. Coll. Cardiol., 2002;39(4):672-675.
Prado et al., "Skeletal muscle anabolism is a side effect of therapy with the MEK inhibitor: selumetinib in patients with cholangiocarcinoma." Br J Cancer. May 8, 2012;106(10):1583-6.
Pulz C et al., (2008), 'Incremental Shuttle and Six-Minute Walking Tests in the Assessment of Functional Capacity in Chronic Heart Failure,' Can J Cardiol, 24(2):131-5.
Riiegg and Glass, "Molecular mechanisms and treatment options for muscle wasting diseases." Annu Rev Pharmacol Toxicol. 2011;51:373-95.
Romano C et al., (2003), 'Reduced Hemodynamic Load and Cardiac Hypotrophy in Patients with Anorexia Nervosa,' Am J Clin Nutr, 77(2):308-12.
Romano et al., "Reduced hemodynamic load and cardiac hypotrophy in patients with anorexia nervosa," Am J Clin Nutr. 2003;77(2):308-312.
Roth et al., "GDF-15 contributes to proliferation and immune escape of malignant gliomas," Clin Cancer Res. Aug. 1, 2010;16(15):3851-9.
Sharma et al., "Molecular targets of cancer cachexia: opportunities for pharmanutritional approaches." PharmaNutrition. 2013 <http://dx.doi.oro/10.1016/i.ohanu.2013.07.002>.
Springer et al. "Prevention of liver cancer cachexia-induced cardiac wasting and heart failure," European Heart Journal 2014;35:932-941.
Steinman and DeBoer, "Chapter 8: Treatment of Cachexia: Melanocortin and Ghrelin Interventions." Vitamins and Hormones. 2013; 92:197-240.
Stewart-Coats et al., "The ACT-ONE trial, a multicentre, randomised, double-blind, placebocontrolled, dose-finding study of the anabolic/catabolic transforming agent, MT-102 in subjects cachexia related to stage III and IV non-small cell lung cancer and colorectal cancer:study design." J Cachexia Sarcopenia Muscle. Dec. 2011;2(4):201-207.
Strassmann et al., Mechanisms of experimental cancer cachexia. Local involvement of IL-1 in colon-26 tumor. J Immunol. Mar. 15, 1993;150(6):2341-5.
Strunk A et al., (2006), 'Impact of the History of Congestive Heart Failure on the Utility of B-Type Natriuretic Peptide in the Emergency Diagnosis of Heart Failure: Results from the Breathing Not Properly Multinational Study,' Am J Med, 119(10):69.e1-11.
Sutton et al. (2003, Circulation 107(15):1985-1990).
Temel et al., "Efficacy and safety results from a phase II study of anamorelin HCI, a ghrelin receptor agonist, in NSCLC patients." J. Cachexia Sarcopenia Muscle 2013;4:295-343 Abstract 5-01 from 7th Cachexia Conference, Kobe/Osaka, Japan, Dec. 9-11, 2013.
Thomas, "Loss of skeletal muscle mass in aging: examining the relationship of starvation, sarcopenia and cachexia." Clin Nutr. Aug. 2007;26(4):389-99.
Tisdale, "Cachexia in cancer patients." Nat Rev Cancer. Nov. 2002;2(11):862-71.
Tobin JF and Celeste AJ, (2006), 'Bone Morphogenetic Proteins and Growth Differentiation Factors as Drug Targets in Cardiovascular and Metabolic Disease,' Drug Discov Today, 11(9-10):405-11.
Tsai et al., "Anorexia/cachexia of chronic diseases: a role for the TGF-13 family cytokine MIC-1/GDF15." J Cachexia Sarcopenia Muscle. Dec. 2012;3(4):239-43.
Tsai VW-Wet al., (2013), 'TGFb Superfamily Cytokine MIC-1/GDF15 is a Physiological Appetite and Body Weight Regulator,' PLOSOne, 8(2):e55174 (10 pages).
Tuca et al., "Clinical evaluation and optimal management of cancer cachexia." Crit Rev Oncol Hematol. Dec. 2013;88(3):625-36.
Wallentin L et al., (2013), 'GDF-15 for Prognostication of Cardiovascular and Cancer Morbidity and Mortality in Men,' PLoS One, 8(12):e78797.
Wallentin LC et al., (2013), 'GDF-15 Level in Acute Coronary Syndrome and its Relations to Cardiovascular Risk Factors, Disease Manifestations, Treatments and Outcome—Results from the PLATO-Study,' Eur Heart J, 34(Suppl 1):P4048 (Abstract).
Wilson JR et al., (1995), 'Dissociation Between Peak Exercise Oxygen Consumption and Hemodynamic Dysfunction in Potential Heart Transplant Candidates,' J Am Coll Cardiol, 26(2):429-35.
Winter et al., (1993), "Humanized antibodies," Trends Pharmacol Sci., 14:139-43.
Wollert KC and Kempf T, (2012), 'Growth Differentiation Factor 15 in Heart Failure: An Update,' Curr Heart Fail Rep, 9(4):337-45.
Written Opinion of the International Searching Authority (Form ISA/237) for Intentional Application No. PCT/US2015/036790 mailed Nov. 30, 2015 (8 pages).

(56) References Cited

OTHER PUBLICATIONS

Xu, Jian et al. "GDF15/MIC-1 functions as a protective and antihypertrophic factor released from the myocardium in association with SMAD protein activation." Circulation research vol. 98,3 (2006): 342-50.
Zhang et al., "Serendipitous discovery of novel imidazolopyrazole scaffold as selective androgen receptor modulators." Bioorg Med Chem Lett. Jan. 15, 2007;17(2):439-43.
Zhang et al., "Synthesis and SAR of novel hydantoin derivatives as selective androgen receptor modulators." Bioorg Med Chem Lett. Nov. 15, 2006;16(22):5763-6.
Zhou et al., "Reversal of cancer cachexia and muscle wasting by ActRIIB antagonism leads to prolonged survival." Cell. Aug. 20, 2010;142(4):531-43.

* cited by examiner

NON CHF: N=45

CHF WITHOUT CACHEXIA (CHF); N=167

CHF WITH CACHEXIA (CHF Ca); N=33

AVERAGE GDF-15 SERUM LEVELS INCREASE WITH SEVERITY OF CHF

NYHA I: 16

NYHA II: 102

NYHA III-IV: 80

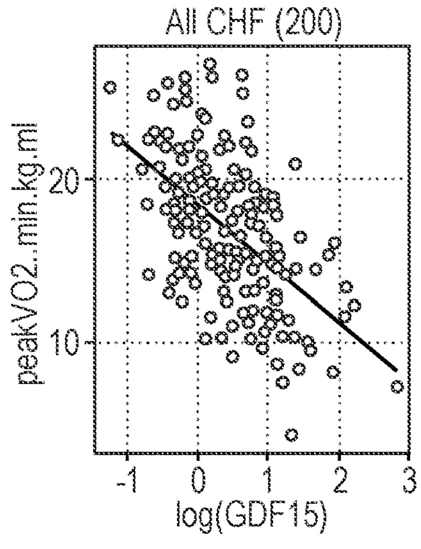

| Type | Annotation | R | P-Val |
|---|---|---|---|
| perf | peakVO2..min.kg.ml | -0.62 | 1E-07 |
| perf | X6.minute.walk..m. | -0.49 | 0.142 |
| perf | gait.speed..m.s. | -0.49 | 0.142 |
| perf | hand.grip.strength.right..kg. | 0.33 | 0.436 |
| perf | leg.grip.strength.right..kg. | -0.20 | 0.546 |
| perf | hand.grip.strength.left..kg. | 0.23 | 0.677 |
| perf | leg.grip.strength.left..kg. | 0.31 | 0.736 |

FIG. 3A

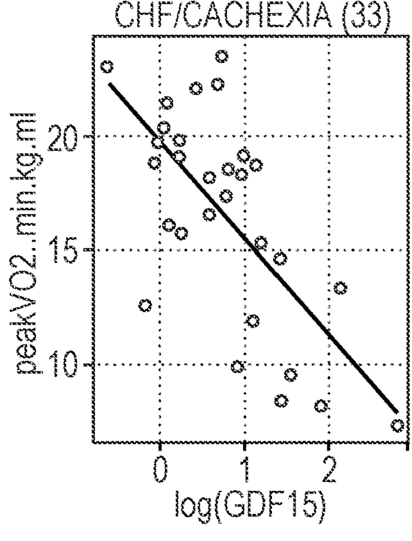

| Type | Annotation | R | P-Val |
|---|---|---|---|
| perf | peakVO2..min.kg.ml | -0.69 | 0.002 |
| perf | hand.grip.strenght.right..kg. | 0.52 | 0.343 |
| perf | leg.grip.strenght.right..kg. | -0.32 | 0.398 |
| perf | gait.speed..m.s. | -0.70 | 0.487 |
| perf | X6.minute.walk..m. | -0.70 | 0.487 |
| perf | hand.grip.strenght.left..kg. | -0.43 | 0.727 |
| perf | leg.grip.strenght.left..kg. | -0.62 | 0.887 |

FIG. 3B

CHF/NON-CACHEXIA (167)
peakVO2..min.kg.ml
20
10
-1
0
1
2
log(GDF15)

| Type | Annotation | R | P-Val |
|---|---|---|---|
| perf | peakVO2..min.kg.ml | -0.62 | 5E-06 |
| perf | X6.minute.walk..m. | -0.46 | 0.143 |
| perf | gait.speed..m.s. | -0.46 | 0.143 |
| perf | hand.grip.strenght.left..kg. | 0.20 | 0.330 |
| perf | leg.grip.strenght.left..kg. | 0.27 | 0.353 |
| perf | hand.grip.strenght.right..kg. | 0.30 | 0.489 |
| perf | leg.grip.strenght.right..kg. | -0.21 | 0.972 |

FIG. 3C

| Type | Annotation | R | P-Val |
|---|---|---|---|
| anemia | TSAT.... | -0.38 | 7E-05 |
| anemia | Iron | -0.31 | 0.001 |
| anemia | Transferrin | 0.26 | 0.017 |
| anemia | Hb..g.dl. | -0.18 | 0.024 |
| anemia | Erythrocyte | -0.08 | 0.267 |
| anemia | Ferritin | -0.13 | 0.363 |

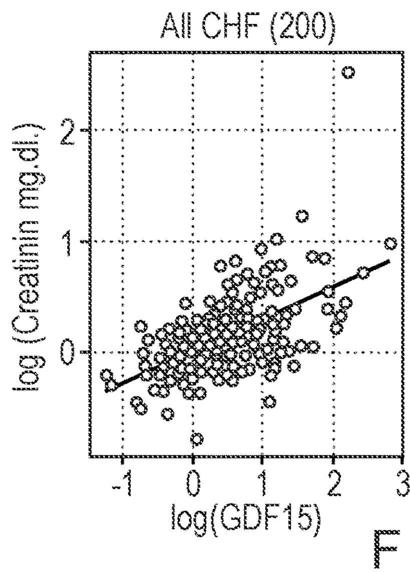

| Type | Annotation | R | P-Val |
|---|---|---|---|
| kidney | Creatinin..mg.dl. | 0.56 | 1E-14 |
| kidney | Urea..mg.dl. | 0.58 | 4E-14 |
| kidney | GFR | -0.54 | 3E-10 |
| kidney | Uric.acid..mg.dl. | 0.47 | 8E-10 |
| kidney | Anorg..Phosphat | 0.24 | 0.112 |
| kidney | Potassium | 0.07 | 0.333 |
| kidney | Calcium | -0.14 | 0.446 |
| kidney | Chlorid | -0.07 | 0.543 |
| kidney | Sodium | 0.04 | 0.835 |

FIG. 5A

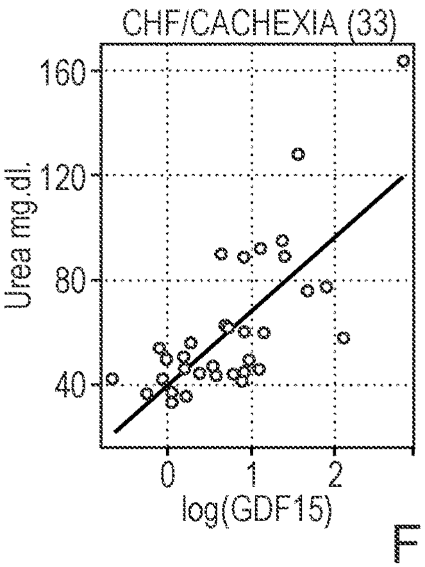

| Type | Annotation | R | P-Val |
|---|---|---|---|
| kidney | Urea..mg.dl. | 0.74 | 7E-06 |
| kidney | Creatinin..mg.dl. | 0.72 | 3E-05 |
| kidney | GFR | -0.67 | 0.001 |
| kidney | Uric.acid..mg.dl. | 0.53 | 0.007 |
| kidney | Anorg..Phosphat | 0.43 | 0.017 |
| kidney | Calcium | 0.29 | 0.159 |
| kidney | Sodium | 0.14 | 0.507 |
| kidney | Potassium | 0.10 | 0.605 |
| kidney | Chlorid | 0.10 | 0.964 |

FIG. 5B

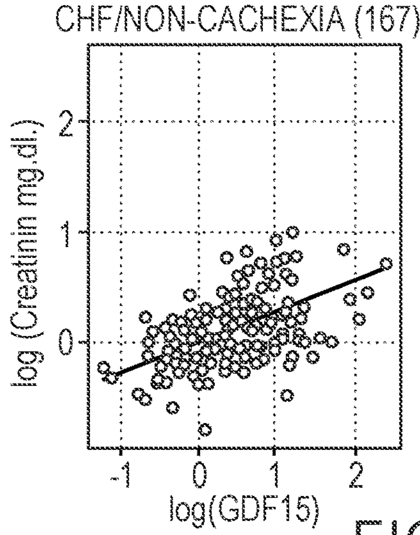

| Type | Annotation | R | P-Val |
|---|---|---|---|
| kidney | Creatinin..mg.dl. | 0.51 | 2E-10 |
| kidney | Urea..mg.dl. | 0.54 | 1E-09 |
| kidney | Uric.acid..mg.dl. | 0.45 | 1E-07 |
| kidney | GFR | -0.49 | 9E-07 |
| kidney | Potassium | 0.10 | 0.250 |
| kidney | Calcium | -0.16 | 0.288 |
| kidney | Chlorid | -0.07 | 0.497 |
| kidney | Anorg..Phosphat | 0.28 | 0.587 |
| kidney | Sodium | 0.04 | 0.899 |

FIG. 5C

SEQUENCE LISTING

```
<160> NUMBER OF SEQ ID NOS: 57

<210> SEQ ID NO 1
<211> LENGTH: 5
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Asp Tyr Asn Met Asp
1               5


<210> SEQ ID NO 2
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 2

Thr Tyr Gly Met Gly Val Ser
1               5


<210> SEQ ID NO 3
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Thr Tyr Gly Met Gly Val Gly
1               5


<210> SEQ ID NO 4
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4
```

-continued

```
Gln Ile Asn Pro Asn Asn Gly Gly Ile Phe Phe Asn Gln Lys Phe Lys
1               5                   10                  15

Gly


<210> SEQ ID NO 5
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 5

Gln Ile Asn Pro Asn Asn Gly Gly Ile Phe Phe Asn Gln Lys Phe Gln
1               5                   10                  15

Gly


<210> SEQ ID NO 6
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 6

Gln Ile Asn Pro Tyr Asn His Leu Ile Phe Phe Asn Gln Lys Phe Gln
1               5                   10                  15

Gly


<210> SEQ ID NO 7
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 7

Gln Ile Asn Pro Asn Asn Gly Leu Ile Phe Phe Asn Gln Lys Phe Gln
1               5                   10                  15

Gly


<210> SEQ ID NO 8
<211> LENGTH: 17
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 8

Gln Ile Asn Pro Asn Asn Gly Leu Ile Phe Phe Asn Gln Lys Phe Lys
1               5                   10                  15

Gly


<210> SEQ ID NO 9
<211> LENGTH: 17
<212> TYPE: PRT
<213> ORGANISM: Artificial Sequence
```

```
<220> FEATURE:
<221> NAME/KEY: source
<223> OTHER INFORMATION: /note="Description of Artificial Sequence:
      Synthetic peptide"

<400> SEQUENCE: 9

Gln Ile Asn Pro Tyr Asn His Leu Ile Phe Phe Asn Gln Lys Phe Lys
1               5                   10                  15

Gly


<210> SEQ ID NO 10
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 10

His Ile Tyr Trp Asp Asp Asp Lys Arg Tyr Asn Pro Ser Leu Lys Ser
1               5                   10                  15


<210> SEQ ID NO 11
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 11

His Ile Tyr Trp Asp Asp Asp Lys Arg Tyr Asn Pro Ser Leu Lys Thr
1               5                   10                  15


<210> SEQ ID NO 12
<211> LENGTH: 16
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 12

Asp Ile Trp Trp Asp Asp Asp Lys Tyr Tyr Asn Pro Ser Leu Lys Ser
1               5                   10                  15


<210> SEQ ID NO 13
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 13

Glu Ala Ile Thr Thr Val Gly Ala Met Asp Tyr
1               5                   10


<210> SEQ ID NO 14
<211> LENGTH: 9
<212> TYPE: PRT
<213> ORGANISM: Artificial Sequence
<220> FEATURE:
<221> NAME/KEY: source
```

```
<223> OTHER INFORMATION: /note="Description of Artificial Sequence:
      Synthetic peptide"

<400> SEQUENCE: 14

Arg Gly Tyr Asp Asp Tyr Trp Gly Tyr
1               5


<210> SEQ ID NO 15
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 15

Arg Gly His Tyr Ser Ala Met Asp Tyr
1               5


<210> SEQ ID NO 16
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 16

Arg Thr Ser Glu Asn Leu His Asn Tyr Leu Ala
1               5                   10


<210> SEQ ID NO 17
<211> LENGTH: 11
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 17

Lys Ala Ser Gln Asn Val Gly Thr Asn Val Ala
1               5                   10


<210> SEQ ID NO 18
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 18

Asp Ala Lys Thr Leu Ala Asp
1               5


<210> SEQ ID NO 19
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 19
```

```
Ser Ala Ser Tyr Arg Tyr Ser
1               5


<210> SEQ ID NO 20
<211> LENGTH: 7
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 20

Ser Pro Ser Tyr Arg Tyr Ser
1               5


<210> SEQ ID NO 21
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 21

Gln His Phe Trp Ser Ser Pro Tyr Thr
1               5


<210> SEQ ID NO 22
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 22

Gln His Phe Trp Ser Asp Pro Tyr Thr
1               5


<210> SEQ ID NO 23
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 23

Gln Gln Tyr Asn Asn Tyr Pro Leu Thr
1               5


<210> SEQ ID NO 24
<211> LENGTH: 9
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 24

Gln Gln Tyr Asn Ser Tyr Pro His Thr
1               5
```

```
<210> SEQ ID NO 25
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 25

Asp Ile Gln Met Thr Gln Ser Pro Ala Ser Leu Ser Ala Ser Val Gly
1               5                   10                  15

Glu Thr Val Thr Ile Thr Cys Arg Thr Ser Glu Asn Leu His Asn Tyr
            20                  25                  30

Leu Ala Trp Tyr Gln Gln Lys Gln Gly Lys Ser Pro Gln Leu Leu Val
        35                  40                  45

Tyr Asp Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ser Tyr Tyr Cys Gln His Phe Trp Ser Ser Pro Tyr
                85                  90                  95

Thr Phe Gly Gly Gly Thr Lys Leu Glu Ile Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210


<210> SEQ ID NO 26
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 26

Asp Ile Gln Met Thr Gln Ser Pro Ala Ser Leu Ser Ala Ser Val Gly
1               5                   10                  15

Glu Thr Val Thr Ile Thr Cys Arg Thr Ser Glu Asn Leu His Asn Tyr
            20                  25                  30

Leu Ala Trp Tyr Gln Gln Lys Gln Gly Lys Ser Pro Gln Leu Leu Val
        35                  40                  45

Tyr Asp Ala Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
```

```
65                  70                  75                  80

Glu Asp Phe Gly Ser Tyr Tyr Cys Gln His Phe Trp Ser Ser Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 27
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 27

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Leu His Asn Tyr
            20                  25                  30

Leu Ala Trp Tyr Gln Gln Lys Pro Gly Lys Ser Pro Lys Leu Leu Val
        35                  40                  45

Tyr Asp Ala Lys Thr Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Ser Ser Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205
```

```
Phe Asn Arg Gly Glu Cys
    210


<210> SEQ ID NO 28
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 28

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Leu His Asn Tyr
            20                  25                  30

Leu Ala Trp Tyr Gln Gln Lys Pro Gly Lys Ser Pro Lys Leu Leu Ile
        35                  40                  45

Tyr Asp Ala Lys Thr Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Ser Ser Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 29
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Leu His Asn Tyr
            20                  25                  30

Leu Ala Trp Tyr Gln Gln Lys Pro Gly Lys Ala Pro Lys Leu Leu Ile
        35                  40                  45
```

```
Tyr Asp Ala Lys Thr Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Ser Ser Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 30
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 30

```
Asp Ile Gln Met Thr Gln Ser Pro Ser Ser Leu Ser Ala Ser Val Gly
1               5                   10                  15

Asp Arg Val Thr Ile Thr Cys Arg Thr Ser Glu Asn Leu His Asn Tyr
            20                  25                  30

Leu Ala Trp Tyr Gln Gln Lys Pro Gly Lys Ser Pro Lys Leu Leu Ile
        35                  40                  45

Tyr Asp Ala Lys Thr Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Tyr Cys Gln His Phe Trp Ser Asp Pro Tyr
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
```

```
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 31
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 31

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Phe Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Ile Leu Thr Ile Ser Asn Val Gln Ser
65                  70                  75                  80

Glu Asp Leu Ala Glu Tyr Phe Cys Gln Gln Tyr Asn Asn Tyr Pro Leu
                85                  90                  95

Thr Phe Gly Ala Gly Thr Lys Leu Glu Leu Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210


<210> SEQ ID NO 32
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 32

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30
```

```
Val Ala Trp Phe Gln Gln Lys Pro Gly Gln Ser Pro Lys Ala Leu Ile
        35                  40                  45

Tyr Ser Ala Ser Tyr Arg Tyr Ser Gly Val Pro Asp Arg Phe Thr Gly
    50                  55                  60

Ser Gly Ser Gly Thr Asp Phe Ile Leu Thr Ile Ser Asn Val Gln Ser
65                  70                  75                  80

Glu Asp Leu Ala Glu Tyr Phe Cys Gln Gln Tyr Asn Asn Tyr Pro Leu
                85                  90                  95

Thr Phe Gly Ala Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 33
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 33

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Phe Gln Gln Lys Pro Gly Lys Ala Pro Lys Ser Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Asn Asn Tyr Pro Leu
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160
```

```
Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 34
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 34

Asp Ile Val Met Thr Gln Ser Gln Lys Phe Met Ser Thr Ser Val Gly
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Pro Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro His
                85                  90                  95

Thr Phe Gly Gly Gly Thr Lys Leu Glu Met Lys Arg Ala Asp Ala Ala
            100                 105                 110

Pro Thr Val Ser Ile Phe Pro Pro Ser Ser Glu Gln Leu Thr Ser Gly
        115                 120                 125

Gly Ala Ser Val Val Cys Phe Leu Asn Asn Phe Tyr Pro Lys Asp Ile
    130                 135                 140

Asn Val Lys Trp Lys Ile Asp Gly Ser Glu Arg Gln Asn Gly Val Leu
145                 150                 155                 160

Asn Ser Trp Thr Asp Gln Asp Ser Lys Asp Ser Thr Tyr Ser Met Ser
                165                 170                 175

Ser Thr Leu Thr Leu Thr Lys Asp Glu Tyr Glu Arg His Asn Ser Tyr
            180                 185                 190

Thr Cys Glu Ala Thr His Lys Thr Ser Thr Ser Pro Ile Val Lys Ser
        195                 200                 205

Phe Asn Arg Asn Glu Cys
    210


<210> SEQ ID NO 35
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 35

Asp Ile Val Met Thr Gln Ser Gln Lys Phe Met Ser Thr Ser Val Gly
```

```
1               5                   10                  15

Asp Arg Val Ser Val Thr Cys Lys Ala Ser Gln Asn Val Gly Thr Asn
            20                  25                  30

Val Ala Trp Tyr Gln Gln Lys Pro Gly Gln Ser Pro Lys Ala Leu Ile
        35                  40                  45

Tyr Ser Pro Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Tyr Phe Cys Gln Gln Tyr Asn Ser Tyr Pro His
                85                  90                  95

Thr Phe Gly Gly Gly Thr Lys Leu Glu Met Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 36
<211> LENGTH: 214
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asn Val Gly Thr Asn
            20                  25                  30

Val Ala Trp Phe Gln Gln Lys Pro Gly Lys Ser Pro Lys Ala Leu Ile
        35                  40                  45

Tyr Ser Pro Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Phe Cys Gln Gln Tyr Asn Ser Tyr Pro His
                85                  90                  95

Thr Phe Gly Gln Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 37
<211> LENGTH: 444
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 37

Glu Val Leu Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Gln Ile Asn Pro Asn Asn Gly Gly Ile Phe Phe Asn Gln Lys Phe
    50                  55                  60

Lys Gly Lys Ala Thr Leu Thr Val Asp Lys Ser Ser Asn Thr Ala Phe
65                  70                  75                  80

Met Glu Val Arg Ser Leu Thr Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Ser Val Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Thr Trp Pro Ser Glu Thr Val Thr Cys Asn Val Ala His Pro Ala
        195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
            260                 265                 270
```

```
Ser Trp Phe Val Asp Asp Val Glu Val His Thr Ala Gln Thr Gln Pro
        275                 280                 285

Arg Glu Glu Gln Phe Asn Ser Thr Phe Arg Ser Val Ser Glu Leu Pro
    290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
        355                 360                 365

Phe Phe Pro Glu Asp Ile Thr Val Glu Trp Gln Trp Asn Gly Gln Pro
    370                 375                 380

Ala Glu Asn Tyr Lys Asn Thr Gln Pro Ile Met Asp Thr Asp Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
            420                 425                 430

His Thr Glu Lys Ser Leu Ser His Ser Pro Gly Lys
        435                 440


<210> SEQ ID NO 38
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 38

Glu Val Leu Leu Gln Gln Ser Gly Pro Glu Leu Val Lys Pro Gly Ala
1               5                   10                  15

Ser Val Lys Ile Pro Cys Lys Ala Ser Gly Tyr Thr Phe Thr Asp Tyr
            20                  25                  30

Asn Met Asp Trp Val Lys Gln Ser His Gly Lys Ser Leu Glu Trp Ile
        35                  40                  45

Gly Gln Ile Asn Pro Asn Asn Gly Gly Ile Phe Phe Asn Gln Lys Phe
    50                  55                  60

Lys Gly Lys Ala Thr Leu Thr Val Asp Lys Ser Ser Asn Thr Ala Phe
65                  70                  75                  80

Met Glu Val Arg Ser Leu Thr Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Ser Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
```

```
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 39
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Lys Ser Leu Glu Trp Ile
        35                  40                  45

Gly Gln Ile Asn Pro Asn Asn Gly Gly Ile Phe Phe Asn Gln Lys Phe
    50                  55                  60

Lys Gly Arg Ala Thr Leu Thr Val Asp Thr Ser Thr Asn Thr Ala Tyr
65                  70                  75                  80
```

```
Met Glu Leu Arg Ser Leu Arg Ser Asp Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 40
<211> LENGTH: 450
<212> TYPE: PRT
<213> ORGANISM: Artificial Sequence
<220> FEATURE:

```
<221> NAME/KEY: source
<223> OTHER INFORMATION: /note="Description of Artificial Sequence:
      Synthetic polypeptide"

<400> SEQUENCE: 40

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Lys Ser Leu Glu Trp Ile
        35                  40                  45

Gly Gln Ile Asn Pro Asn Asn Gly Gly Ile Phe Phe Asn Gln Lys Phe
    50                  55                  60

Lys Gly Arg Ala Thr Leu Thr Val Asp Lys Ser Thr Asn Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
```

```
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 41
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 41

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Gln Gly Leu Glu Trp Met
        35                  40                  45

Gly Gln Ile Asn Pro Asn Asn Gly Gly Ile Phe Phe Asn Gln Lys Phe
    50                  55                  60

Lys Gly Arg Val Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285
```

```
Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 42
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Gln Gly Leu Glu Trp Met
        35                  40                  45

Gly Gln Ile Asn Pro Asn Asn Gly Gly Ile Phe Phe Asn Gln Lys Phe
    50                  55                  60

Gln Gly Arg Val Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 43
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Gln Ser Leu Glu Trp Met
        35                  40                  45

Gly Gln Ile Asn Pro Asn Asn Gly Gly Ile Phe Phe Asn Gln Lys Phe
    50                  55                  60

Gln Gly Arg Val Thr Leu Thr Thr Asp Thr Ser Thr Ser Thr Ala Tyr
```

```
65                  70                  75                  80

Met Glu Leu Arg Ser Leu Arg Ser Asp Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 44
<211> LENGTH: 450
<212> TYPE: PRT
<213> ORGANISM: Artificial Sequence

```
<220> FEATURE:
<221> NAME/KEY: source
<223> OTHER INFORMATION: /note="Description of Artificial Sequence:
      Synthetic polypeptide"

<400> SEQUENCE: 44

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
            20                  25                  30

Asn Met Asp Trp Val Arg Gln Ala Pro Gly Gln Gly Leu Glu Trp Met
        35                  40                  45

Gly Gln Ile Asn Pro Asn Asn Gly Gly Ile Phe Phe Asn Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380
```

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 45
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 45

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
            20                  25                  30

Asn Met Asp Trp Val Arg Gln Ala Pro Gly Gln Gly Leu Glu Trp Met
        35                  40                  45

Gly Gln Ile Asn Pro Asn Asn Gly Gly Ile Phe Phe Asn Gln Lys Phe
    50                  55                  60

Gln Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
```

```
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 46
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 46

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Gln Ser Leu Glu Trp Met
        35                  40                  45

Gly Gln Ile Asn Pro Tyr Asn His Leu Ile Phe Phe Asn Gln Lys Phe
    50                  55                  60

Gln Gly Arg Val Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 47
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 47

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asp Tyr
            20                  25                  30

Asn Met Asp Trp Val Arg Gln Ala Pro Gly Gln Ser Leu Glu Trp Met
        35                  40                  45

Gly Gln Ile Asn Pro Asn Asn Gly Leu Ile Phe Phe Asn Gln Lys Phe
    50                  55                  60
```

```
Gln Gly Arg Val Thr Leu Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450
```

<210> SEQ ID NO 48
<211> LENGTH: 450
<212> TYPE: PRT

<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 48

```
Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
            20                  25                  30

Asn Met Asp Trp Val Arg Gln Ala Pro Gly Gln Gly Leu Glu Trp Met
        35                  40                  45

Gly Gln Ile Asn Pro Asn Asn Gly Leu Ile Phe Phe Asn Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380
```

```
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 49
<211> LENGTH: 450
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 49

Gln Val Gln Leu Val Gln Ser Gly Ala Glu Val Lys Lys Pro Gly Ser
1               5                   10                  15

Ser Val Lys Val Ser Cys Lys Ala Ser Gly Tyr Thr Phe Ser Asp Tyr
            20                  25                  30

Asn Met Asp Trp Val Arg Gln Ala Pro Gly Gln Gly Leu Glu Trp Met
        35                  40                  45

Gly Gln Ile Asn Pro Tyr Asn His Leu Ile Phe Phe Asn Gln Lys Phe
    50                  55                  60

Lys Gly Arg Val Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Ala Ile Thr Thr Val Gly Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270
```

```
Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450


<210> SEQ ID NO 50
<211> LENGTH: 443
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 50

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Asn Thr Tyr
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Ala Ser Asn Asn Arg Val
65                  70                  75                  80

Phe Leu Lys Ile Thr Ser Val Asp Thr Ala Asp Thr Ala Thr Tyr Tyr
                85                  90                  95

Cys Ala Gln Arg Gly Tyr Asp Asp Tyr Trp Gly Tyr Trp Gly Gln Gly
            100                 105                 110

Thr Leu Val Thr Ile Ser Ala Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
```

```
                165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
    290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Pro Lys Glu
            340                 345                 350

Gln Met Ala Lys Asp Lys Val Ser Leu Thr Cys Met Ile Thr Asp Phe
        355                 360                 365

Phe Pro Glu Asp Ile Thr Val Glu Trp Gln Trp Asn Gly Gln Pro Ala
    370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
        435                 440
```

<210> SEQ ID NO 51
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 51

```
Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Asn Thr Tyr
            20                  25                  30

Gly Met Gly Val Ser Trp Ile Arg Gln Pro Pro Gly Lys Ala Leu Glu
        35                  40                  45

Trp Leu Ala His Ile Tyr Trp Asp Asp Asp Lys Arg Tyr Asn Pro Ser
    50                  55                  60

Leu Lys Thr Arg Leu Thr Ile Ser Lys Asp Thr Ser Lys Asn Gln Val
65                  70                  75                  80
```

```
Val Leu Thr Ile Thr Asn Val Asp Pro Val Asp Thr Ala Val Tyr Tyr
                85                  90                  95

Cys Ala Gln Arg Gly Tyr Asp Asp Tyr Trp Gly Tyr Trp Gly Gln Gly
            100                 105                 110

Thr Leu Val Thr Ile Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

<210> SEQ ID NO 52
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 52

```
Gln Val Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Asn Thr Tyr
            20                  25                  30

Gly Met Gly Val Ser Trp Ile Arg Gln Pro Pro Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Thr Lys Asp Thr Ser Lys Asn Gln Val
65                  70                  75                  80

Val Leu Thr Ile Thr Asn Met Asp Pro Val Asp Thr Ala Thr Tyr Tyr
                85                  90                  95

Cys Ala Gln Arg Gly Tyr Asp Asp Tyr Trp Gly Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400
```

```
Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 53
<211> LENGTH: 443
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 53

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Met Gly Val Gly Trp Ile Arg Gln Pro Ser Gly Lys Gly Leu Glu
        35                  40                  45

Trp Leu Ala Asp Ile Trp Trp Asp Asp Asp Lys Tyr Tyr Asn Pro Ser
    50                  55                  60

Leu Lys Ser Arg Leu Thr Ile Ser Lys Asp Thr Ser Ser Asn Glu Val
65                  70                  75                  80

Phe Leu Lys Ile Ala Ile Val Asp Thr Ala Asp Thr Ala Thr Tyr Tyr
                85                  90                  95

Cys Ala Arg Arg Gly His Tyr Ser Ala Met Asp Tyr Trp Gly Gln Gly
            100                 105                 110

Thr Ser Val Thr Val Ser Ser Ala Lys Thr Thr Pro Pro Ser Val Tyr
        115                 120                 125

Pro Leu Ala Pro Gly Ser Ala Ala Gln Thr Asn Ser Met Val Thr Leu
    130                 135                 140

Gly Cys Leu Val Lys Gly Tyr Phe Pro Glu Pro Val Thr Val Thr Trp
145                 150                 155                 160

Asn Ser Gly Ser Leu Ser Ser Gly Val His Thr Phe Pro Ala Val Leu
                165                 170                 175

Gln Ser Asp Leu Tyr Thr Leu Ser Ser Ser Val Thr Val Pro Ser Ser
            180                 185                 190

Thr Trp Pro Ser Glu Thr Val Thr Cys Asn Val Ala His Pro Ala Ser
        195                 200                 205

Ser Thr Lys Val Asp Lys Lys Ile Val Pro Arg Asp Cys Gly Cys Lys
    210                 215                 220

Pro Cys Ile Cys Thr Val Pro Glu Val Ser Ser Val Phe Ile Phe Pro
225                 230                 235                 240

Pro Lys Pro Lys Asp Val Leu Thr Ile Thr Leu Thr Pro Lys Val Thr
                245                 250                 255

Cys Val Val Val Asp Ile Ser Lys Asp Asp Pro Glu Val Gln Phe Ser
            260                 265                 270

Trp Phe Val Asp Asp Val Glu Val His Thr Ala Gln Thr Gln Pro Arg
        275                 280                 285

Glu Glu Gln Phe Asn Ser Thr Phe Arg Ser Val Ser Glu Leu Pro Ile
```

```
    290                 295                 300

Met His Gln Asp Trp Leu Asn Gly Lys Glu Phe Lys Cys Arg Val Asn
305                 310                 315                 320

Ser Ala Ala Phe Pro Ala Pro Ile Glu Lys Thr Ile Ser Lys Thr Lys
                325                 330                 335

Gly Arg Pro Lys Ala Pro Gln Val Tyr Thr Ile Pro Pro Pro Lys Glu
            340                 345                 350

Gln Met Ala Lys Asp Lys Val Ser Leu Thr Cys Met Ile Thr Asp Phe
        355                 360                 365

Phe Pro Glu Asp Ile Thr Val Glu Trp Gln Trp Asn Gly Gln Pro Ala
    370                 375                 380

Glu Asn Tyr Lys Asn Thr Gln Pro Ile Met Asp Thr Asp Gly Ser Tyr
385                 390                 395                 400

Phe Val Tyr Ser Lys Leu Asn Val Gln Lys Ser Asn Trp Glu Ala Gly
                405                 410                 415

Asn Thr Phe Thr Cys Ser Val Leu His Glu Gly Leu His Asn His His
            420                 425                 430

Thr Glu Lys Ser Leu Ser His Ser Pro Gly Lys
        435                 440


<210> SEQ ID NO 54
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 54

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Tyr
            20                  25                  30

Gly Met Gly Val Gly Trp Ile Arg Gln Pro Ser Gly Lys Gly Leu Glu
        35                  40                  45

Trp Leu Ala Asp Ile Trp Trp Asp Asp Asp Lys Tyr Tyr Asn Pro Ser
    50                  55                  60

Leu Lys Ser Arg Leu Thr Ile Ser Lys Asp Thr Ser Ser Asn Glu Val
65                  70                  75                  80

Phe Leu Lys Ile Ala Ile Val Asp Thr Ala Asp Thr Ala Thr Tyr Tyr
                85                  90                  95

Cys Ala Arg Arg Gly His Tyr Ser Ala Met Asp Tyr Trp Gly Gln Gly
            100                 105                 110

Thr Ser Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205
```

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 55
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence: Synthetic polypeptide"

<400> SEQUENCE: 55

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Asn Thr Tyr
            20                  25                  30

Gly Met Gly Val Ser Trp Ile Arg Gln Pro Ser Gly Lys Gly Leu Glu
        35                  40                  45

Trp Leu Ala His Ile Tyr Trp Asp Asp Asp Lys Arg Tyr Asn Pro Ser
    50                  55                  60

Leu Lys Ser Arg Leu Thr Ile Ser Lys Asp Ala Ser Asn Asn Arg Val
65                  70                  75                  80

Phe Leu Lys Ile Thr Ser Val Asp Thr Ala Asp Thr Ala Thr Tyr Tyr
                85                  90                  95

Cys Ala Gln Arg Gly Tyr Asp Asp Tyr Trp Gly Tyr Trp Gly Gln Gly

```
            100                 105                 110

Thr Leu Val Thr Ile Ser Ala Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 56
<211> LENGTH: 447
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 56
```

```
Gln Ile Thr Leu Lys Glu Ser Gly Pro Thr Leu Val Lys Pro Thr Gln
1               5                   10                  15

Thr Leu Thr Leu Thr Cys Thr Phe Ser Gly Phe Ser Leu Ser Thr Tyr
            20                  25                  30

Gly Met Gly Val Gly Trp Ile Arg Gln Pro Pro Gly Lys Ala Leu Glu
        35                  40                  45

Trp Leu Ala Asp Ile Trp Trp Asp Asp Asp Lys Tyr Tyr Asn Pro Ser
    50                  55                  60

Leu Lys Ser Arg Leu Thr Ile Thr Lys Asp Thr Ser Lys Asn Gln Val
65                  70                  75                  80

Val Leu Thr Met Thr Asn Met Asp Pro Val Asp Thr Ala Thr Tyr Tyr
                85                  90                  95

Cys Ala Arg Arg Gly His Tyr Ser Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Asn Val Phe Ser Cys Ser Val Met His Glu Ala Leu
```

```
            420                 425                 430

His Asn His Tyr Thr Gln Lys Ser Leu Ser Leu Ser Pro Gly Lys
        435                 440                 445


<210> SEQ ID NO 57
<211> LENGTH: 449
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"

<400> SEQUENCE: 57

Gln Val Thr Leu Lys Glu Ser Gly Pro Ala Leu Val Lys Pro Thr Gln
1               5                   10                  15

Thr Leu Thr Leu Thr Cys Thr Phe Ser Gly Phe Ser Leu Ser Thr Tyr
            20                  25                  30

Gly Met Gly Val Gly Trp Ile Arg Gln Pro Pro Gly Lys Ala Leu Glu
        35                  40                  45

Trp Leu Ala Asp Ile Trp Trp Asp Asp Asp Lys Tyr Tyr Asn Pro Ser
    50                  55                  60

Leu Lys Ser Arg Leu Thr Ile Ser Lys Asp Thr Ser Lys Asn Gln Val
65                  70                  75                  80

Val Leu Thr Met Thr Asn Met Asp Pro Val Asp Thr Ala Val Tyr Tyr
                85                  90                  95

Cys Ala Arg Arg Gly His Tyr Ser Ala Met Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Arg Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335
```

-continued

```
Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys
```

TREATMENT OF CONGESTIVE HEART FAILURE AND OTHER CARDIAC DYSFUNCTION USING A GDF15 MODULATOR

CROSS-REFERENCE TO RELATED APPLICATIONS

This application is a continuation of U.S. patent application Ser. No. 16/177,792, filed Nov. 1, 2018, now abandoned, which is a continuation of U.S. patent application Ser. No. 15/320,094, filed Dec. 19, 2016, now abandoned, which is a U.S. national stage application filed under 35 U.S.C. § 371 of International Patent Application No. PCT/US2015/036790, filed Jun. 19, 2015, which claims priority to and the benefit of U.S. Provisional Patent Application No. 62/015,093, filed Jun. 20, 2014, the entire contents of each of which are incorporated by reference herein in their entireties.

FIELD OF THE INVENTION

The present invention relates to methods of using, and compositions containing, a GDF15 modulator for treating a subject having a cardiac disorder or dysfunction, for example, congestive heart failure, chronic heart failure and acute cardiac conditions such as myocardial infarction.

BACKGROUND OF THE INVENTION

Heart failure, also called congestive heart failure, is a common and expensive condition that is highly debilitating and potentially lethal. It is a leading cause of hospitalization in people aged over 65 years. Heart failure may be the result of rapid onset, termed "acute heart failure" or may develop over long periods of time, termed "chronic heart failure."

Heart failure may be associated with a number of other cardiac conditions, disorders and dysfunctions, including: cardiac arrest or heart stoppage; myocardial infarction (also known as a heart attack) which refers to heart muscle damage, usually due to insufficient blood supply, for example, due to a blocked coronary artery; and cardiomyopathy, referring to damage to heart muscle, which may be genetic, or acquired, and which may be dilated, hypertrophic or restrictive. Dilated cardiomyopathy is primarily genetic in origin, and involves stretching and thinning of the muscle, usually in the left ventricle. When this happens, the heart muscle becomes unable to pump blood efficiently around the body, which can lead to fluid accumulating in the lungs ankles, abdomen and other organs, as well as a feeling of breathlessness. Hypertrophic cardiomyopathy involves thickening of the heart muscle, which may result in myocardial disarray of the cell structure, stiffening of the heart muscle and high blood pressure. Restrictive cardiomyopathy involves a stiffening of the walls of the ventricles, so that they resist normal filling with blood. Restrictive cardiomyopathies can result from a number of causes, such as: hemochromatosis, in which too much iron builds up in the body, which can damage the heart; sarcoidosis, in which abnormal inflammation causes lumps of cells to form in the body's organs, including the heart; and amyloidosis, in which abnormal levels of protein, such as amylin, build up in the organs, including the heart.

Other cardiac-related conditions that may be associated with heart failure include: cardiac hypertrophy, ischemic/reperfusion injury, dyspnea, idiopathic pulmonary arterial hypertension, ST-segment elevation myocardial infarction (STEMI), and cardiovascular dysfunction.

Growth Differentiation Factor-15 (GDF15) is a member of the transforming growth factor-beta (TGF-β) superfamily of proteins, which comprise a large group of multifunctional proteins that serve as regulators of cell proliferation and differentiation. Prominent members of this family include the TGF-βs 1-5, activins, bone morphogenetic proteins (BMPs) that serve as regulators of bone, cartilage and other tissue types, and other proteins involved in cellular regulation, such as glial cell-line derived neurotrophic factor (GDNF), and myostatin (also known as GDF-8). GDF15 was isolated initially from such tissues as prostate and placenta, and has been known by the additional names macrophage inhibitory cytokine 1 (or MIC1), NSAID-activated gene 1 protein (or NAG1), NSAID-regulated gene 1 protein (or NRG-1), placental TGF-beta (or PTGFB), placental bone morphogenetic protein (or PLAB), and prostate differentiation factor (or PDF).

Reports of the activity of GDF15 in subjects with heart injury have been contradictory and inconclusive. Kempf et al. reported that endogenous GDF15 protects the heart from ischemic/reperfusion injury (Kempf et al., 2006, Circulation Research, 98:351-360); and later reported that GDF15 functions as a cardioprotective cytokine during myocardial infarction and heart failure (Kempf et al., 2007, Clinical Chemistry, 53:284-291). See also, Tobin and Celeste, 2006, Drug Discovery Today, 11:405-411; Lajer et al., 2010, Diabetes Care, 33:1567-1572. Breit and Brown, U.S. Pat. No. 7,919,084 postulate treatment of cardiovascular disease by either inhibiting or increasing the activity or expression of GDF15. More recent studies have called for more studies as to whether a causative relationship exists between GDF15 levels and heart failure. See Bonica et al., 2011, Arteriosclerosis, Thrombosis and Vascular Biology, 31:203-210; Wallentin et al., 2013, Eur. Heart J., 34(suppl.):P4048.

Notwithstanding the progress made to date, there still exists a need for better methods of detecting, preventing, and treating cardiac conditions and disorders.

SUMMARY OF THE INVENTION

The present inventors have found that subjects suffering from cardiac conditions and disorders, such as congestive heart failure, that are not effectively or optimally treated with presently available methods surprisingly may be effectively treated with a composition that selectively reduces or inhibits the activity of GDF15. This may be effected by reducing the expression, level or amount, or biological activity, of GDF15 in a subject, which can be measured, for example, in the subject's serum or plasma.

The present invention provides methods and compositions for treating a subject having a cardiovascular disease, congestive or chronic heart failure, myocardial hypertrophy or hypotrophy, acute coronary syndrome, angina, or other cardiac disorder or condition, or who has suffered a cardiac event such as a myocardial infarction, or who has had, or is diagnosed as needing, a cardiac intervention, such as percutaneous coronary intervention, coronary artery bypass grafting, coronary angioplasty or stent placement.

The invention comprises compositions which reduce or inhibit the activity of GDF15, for example, by reducing the ability of GDF15 to bind to an endogenous binding partner (also referred to as cognate receptor or binding partner), for example, by competitively binding to GDF15 or to an endogenous binding partner, or by otherwise neutralizing the activity of GDF15. In certain embodiments, such a composition may comprise an antibody that binds to GDF15 or an endogenous binding partner, as well as a peptide or fusion molecule that comprises such an antibody. In certain other embodiments, the composition may comprise a peptide or small molecule that binds, for example, competitively binds, to GDF15 or to an endogenous binding partner, such that the activity of GDF15 is reduced or inhibited, for example, by reducing or inhibiting the ability of GDF15 to bind to its endogenous binding partner or otherwise neutralizing the activity of GDF15.

In certain embodiments, the invention comprises a method of treating a subject exhibiting one or more cardiac related characteristics, which can be symptoms of cardiovascular disease or dysfunction, congestive or chronic heart failure, cardiac myopathies, cardiac hypertrophy, ischemic/reperfusion injury, dyspnea, idiopathic pulmonary arterial hypertension, ST-segment elevation myocardial infarction (STEMI), or other cardiac disorder or condition.

Such cardiac-related characteristics include:

(1) the subject exhibits reduced or below-normal peak oxygen consumption ($VO_2$);
(2) the subject has elevated or above normal levels of brain natriuretic protein (BNP) or an N-terminal fragment thereof (NT-ProBNP);
(3) the subject has elevated or above normal levels of troponin;
(4) the subject has elevated or above normal levels of C-reactive protein (CRP);
(5) the subject has an abnormal electrocardiogram test, or has been diagnosed as having abnormal physiological heart activity, for example, reduced auricular or ventricular ejection volumes;
(6) the subject exhibits signs or symptoms of chest pain or discomfort (angina), shortness of breath, and fatigue with activity or exertion; or subject exhibits reduced capacity in a test of physical capacity, such as the six minute walking test (6MWT) or incremental shuttle walk test (SWT);
(7) the subject has low normal or below normal levels of heart type fatty acid binding protein (hFABP);
(8) the subject exhibits cardiac hypertrophy or cardiac hypotrophy;
(9) the subject has experienced, or is diagnosed to be at risk of experiencing a myocardial infarction, or thromboembolic stroke; or
(10) the subject has had, or is diagnosed as needing, a coronary intervention, such as percutaneous coronary intervention, coronary artery bypass grafting, coronary angioplasty, stent placement, heart transplant, or defibrillator placement.

The above cardiac-related characteristics can also be used to monitor the subject's progress in response to treatment with a GDF15 modulator in accordance with the present invention, and to modify the dosing regimen if deemed clinically appropriate. In certain embodiments, the subject having a cardiovascular disease or cardiac disorder, such as congestive or chronic heart failure (CHF), has previously been treated with a known cardiac treatment, but persists in exhibiting at least one of the above characteristics. In such cases, the present invention provides methods and compositions for avoiding or reducing the occurrence and/or severity of at least one of the above cardiac-related characteristics, and may also avoid or reduce the need for one of the cardiac interventions described above.

In one aspect, the invention provides a method of improving or increasing cardiac function in a subject in need thereof, the method comprising administering an effective amount of a composition comprising a GDF15 modulator thereby to improve or increase cardiac function in the subject. Cardiac function can include any of the biochemical and physiological parameters discussed below.

In another aspect, the invention provides a method of treating a subject having a cardiac disorder or dysfunction, the method comprising administering an effective amount of a composition comprising a GDF15 modulator thereby to ameliorate a symptom of the cardiac disorder or dysfunction. The symptoms can include any of the biochemical and physiological parameters discussed below.

In another aspect, the invention provides a method of reducing or reversing cardiac hypotrophy in a subject exhibiting one or more symptoms of congestive heart failure, the method comprising administering an effective amount of a composition comprising a GDF15 modulator, wherein the composition ameliorates at least one symptom of cardiac hypotrophy in the subject. The symptoms can include any of the biochemical and physiological parameters discussed below.

In another aspect, the invention provides a method of treating or preventing congestive heart failure in a subject in need thereof, the method comprising administering an effective amount of a composition that reduces or inhibits a GDF15 activity in the subject, thereby to treat or prevent CHF in the subject. The symptoms can include any of the biochemical and physiological parameters discussed below.

In another aspect, the invention provides a method of reducing or reversing cardiac hypotrophy in a subject exhibiting one or more characteristics of congestive heart failure, the method comprising administering an effective amount of a composition that modulates the activity of GDF15, thereby to reduce cardiac hypotrophy in the subject. The symptoms can include any of the biochemical and physiological parameters discussed below.

In certain embodiments, the subject has elevated GDF15 activity in a body fluid, for example, serum or plasma. In certain embodiments, elevated GDF15 activity means elevated GDF15 levels. In certain other embodiments, the subject exhibits a peak $VO_2$ of less than less than 14 mL/kg/min, an LVEF of less than 40%, BNP levels in excess of 100 pg/ml, serum cardiac troponin I (cTnI) levels in excess of 1.5 ng/mL, or any combination of the foregoing. In certain embodiments, the subject has already been diagnosed as having congestive heart failure.

In certain embodiments, the GDF15 modulator of the invention can reduce or inhibit GDF15 activity in the subject. In some embodiments, the GDF15 modulator inhibits the activity, expression or binding of GDF15 to its cognate receptor. In some embodiments, the GDF15 modulator binds GDF15. The GDF15 modulator can be an anti-GDF15 antibody, which can be humanized or human.

In certain embodiments, the subject exhibits above normal levels of a biomarker selected from the group consisting of cardiac troponin I, cardiac troponin T, brain natriuretic protein (BNP), N-terminal peptides derived from BNP (NT-proBNP), and cardiac fatty acid binding protein (cFABP).

Methods according to the invention can include administering an effective amount of a composition that inhibits a GDF15 mediated pathway, thereby to treat a subject having one or more of the following characteristics: cardiac hypertrophy or cardiac hypotrophy; signs or symptoms of chest pain or discomfort (angina), shortness of breath, and fatigue with activity or exertion; peak $VO_2$; elevated or above normal levels of troponin; elevated or above normal levels of brain natriuretic protein (BNP) or an N-terminal fragment thereof (NT-ProBNP); low normal or below normal levels of heart type fatty acid binding protein (hFABP); an abnormal electrocardiogram test or having abnormal heart physiology or activity, for example, reduced auricular or ventricular ejection volume; having experienced, or diagnosed to be at risk for angina, a myocardial infarction, or thromboembolic stroke; or having had or diagnosed as needing, a coronary intervention, such as percutaneous coronary intervention, coronary artery bypass grafting, coronary angioplasty, stent placement, heart transplant, or defibrillator placement.

The use of the GDF15 modulator described herein can be used to improve or ameliorate at least one of the following characteristics in a subject, wherein the subject has been diagnosed as, or considered to be at risk of developing CHF, a cardiac myopathy, or heart failure:

(1) the subject exhibits reduced or below-normal peak oxygen consumption ($VO_2$);

(2) the subject has elevated or above normal levels of brain natriuretic protein (BNP) or an N-terminal fragment thereof (NT-ProBNP);

(3) the subject has elevated or above normal levels of troponin;

(4) the subject has elevated or above normal levels of C-reactive protein (CRP);

(5) the subject has an abnormal electrocardiogram test, or having abnormal heart physiology or activity, for example, reduced auricular or ventricular ejection volume;

(6) the subject exhibits signs or symptoms of chest pain or discomfort (angina), shortness of breath, and fatigue with activity or exertion, or subject exhibits reduced capacity in a test of physical capacity, such as the six minute walking test (6MWT) or incremental shuttle walk test (SWT);

(7) the subject has low normal or below normal levels of heart type fatty acid binding protein (hFABP);

(8) the subject exhibits cardiac hypertrophy or cardiac hypotrophy;

(9) the subject has experienced, or is diagnosed to be at risk of experiencing a myocardial infarction, or thromboembolic stroke; or

(10) the subject has had, or is diagnosed as needing, a coronary intervention, such as percutaneous coronary intervention, coronary artery bypass grafting, coronary angioplasty, stent placement, heart transplant, or defibrillator placement.

The above characteristics can be monitored to confirm the subject's response to treatment with GDF15 modulator in accordance with the present invention, and to modify the dosing regimen if deemed clinically appropriate. In certain embodiments, the subject having a cardiovascular disease or cardiac disorder, such as CHF, has previously been treated with a known treatment, but persists in exhibiting at least one of the above characteristics. In such cases, the present invention provides methods and compositions for avoiding or reducing the occurrence and/or severity of at least one of the above cardiac-related characteristics, and may also avoid or reduce the need for one of the coronary interventions described above. In particular embodiments, the subject exhibits one or more of the following characteristics such that the subject is considered to have or be suffering from CHF, such that the subject may benefit from treatment according to the present invention. As used throughout the application, the term "considered to have CHF" or "considered to be suffering from CHF" means that following the disclosure of this application, one skilled in the art would expect that a subject would benefit from the administration of GDF15 inhibitors in accordance with the present invention. A subject is also "considered to have CHF" or "considered to be suffering from CHF" if a qualified clinical professional, after examination of information related to the subject, has made the professional judgment or diagnosis that the subject presently suffers from CHF. The term "considered to have CHF" or "considered to be suffering from CHF" means that, following the disclosure of this application, one skilled in the art would expect that a subject would benefit from the prophylactic or therapeutic administration of GDF15 inhibitors in accordance with the present invention. A subject is also term "considered to be at risk of developing CHF" if a qualified clinical professional, after examination of information related to the subject, has made the professional judgment or diagnosis that the subject presently a risk of developing CHF, sufficient to justify prophylactic or therapeutic intervention.

BRIEF DESCRIPTION OF THE FIGURES

FIGS. 3A-3C are graphs illustrating the correlation between GDF15 levels and peak volume of oxygen ($VO_2$), which is a marker of cardiac function. Peak $VO_2$ levels decrease with increased GDF15 levels in 200 subjects with CHF (FIG. 3A), comprising 33 subjects with cachexia (FIG. 3B), and 167 subjects without cachexia, as a co-morbidity of CHF (FIG. 3C).

FIGS. 5A-5C are graphs illustrating the correlation between GDF15 levels and various markers of decreased kidney function, which is a frequent co-morbidity of CHF. FIG. 5A shows that creatinine levels are increased with GDF15 levels in 200 subjects with CHF; FIG. 5B shows that urea levels are increased with GDF15 levels in 33 subjects with CHF and cachexia co-morbidity; and FIG. 5C shows that creatinine levels are increased with GDF15 levels in 167 subjects with CHF without cachexia co-morbidity.

DETAILED DESCRIPTION OF THE INVENTION

Figure 1:
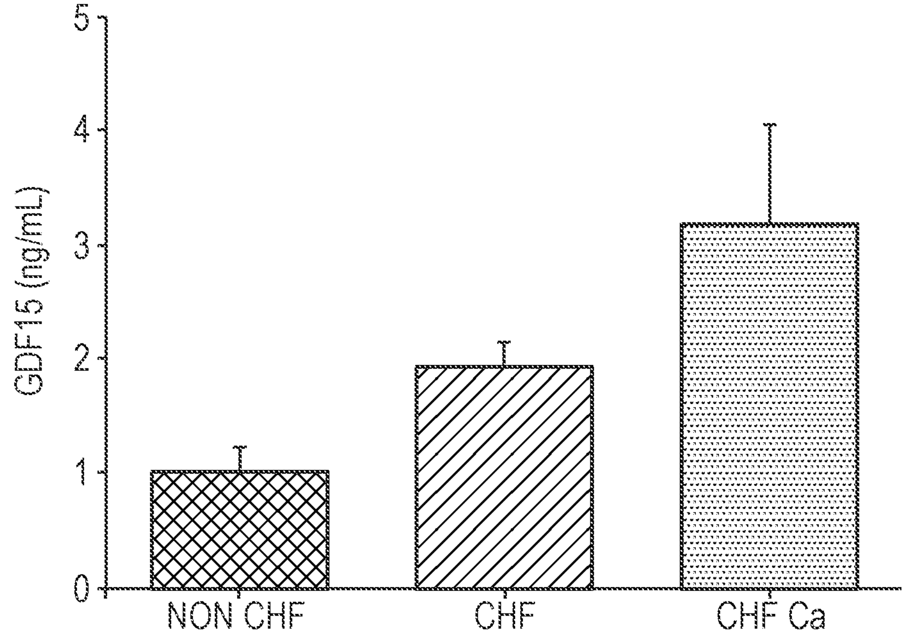
FIG. 1 is a graph illustrating GDF15 levels in human subjects who are not suffering from congestive heart failure ("non-CHF"); subjects who exhibit symptoms of congestive heart failure without cachexia ("CHF"); and subjects who exhibit symptoms of congestive heart failure with cachexia ("CHF Ca").

The present invention provides methods and compositions for treating a subject having a cardiac related disease or disorder, for example, a subject having congestive or chronic heart failure, acute myocardial infarction, myocardial hypertrophy, and myocardial hypotrophy. The methods and compositions may be useful in treating a subject who exhibits at least one characteristic that is symptomatic of a cardiac myopathy or other heart failure, including one or more of:

(1) the subject exhibits reduced or below-normal peak oxygen consumption ($VO_2$);

(2) the subject has elevated or above normal levels of brain natriuretic protein (BNP) or an N-terminal fragment thereof (NT-ProBNP);

(3) the subject has elevated or above normal levels of troponin;

(4) the subject has elevated or above normal levels of C-reactive protein (CRP);

(5) the subject has an abnormal electrocardiogram (ECG) test, or having abnormal heart physiology or activity, for example, reduced auricular or ventricular ejection volume;

(6) the subject exhibits signs or symptoms of chest pain or discomfort (angina), shortness of breath, and fatigue with activity or exertion, or subject exhibits reduced capacity in a test of physical capacity, such as the six minute walking test (6MWT) or incremental shuttle walk test (SWT);

(7) the subject has low normal or below normal levels of heart type fatty acid binding protein (hFABP);

(8) the subject exhibits cardiac hypertrophy or cardiac hypotrophy;

(9) the subject has experienced, or is diagnosed to be at risk of experiencing a myocardial infarction, or thromboembolic stroke; or

(10) the subject has had, or is diagnosed as needing, a coronary intervention, such as percutaneous coronary intervention, coronary artery bypass grafting, coronary angioplasty, stent placement, heart transplant, or defibrillator placement.

Treatment in accordance with the methods and compositions described herein may improve or ameliorate one or more the characteristics or symptoms noted above. As used herein, "treat," "treating" and "treatment" mean the treatment of a disease in a mammal, e.g., in a human. This includes: (a) inhibiting the disease, i.e., arresting its development; and (b) relieving the disease, i.e., causing regression of the disease state.

I. Heart Function Assays

Heart function can be assessed and monitored using a variety of approaches, including physiological and biochemical parameters, symptoms, functional markers and biomarkers of heart function. Physiological and biochemical parameters of heart function can include glomerular filtration rate (GFR); carotid artery ultrasound evaluation; carotid artery IMT (Intima-media thickness) and carotid plaque burden; left ventricular (LV) geometry and function; LV mass index; end-diastolic diameter and LV ejection fraction (echocardiography); forearm blood flow measurements, including endothelium-dependent and independent vasodilation of forearm; flow mediated dilation; and brachial artery ultrasound examination. Further parameters for assessment include cardiac dysfunction or dysrhythmia measured by echocardiography; pulmonary congestion measured by chest x-ray; reduced exercise capacity; abnormal haemodynamics at rest; cardiac output; systemic vascular resistance; left ventricular stroke volume; aortic pressure; left ventricular pressure; peak rate of change of left ventricular pressure during isovolumic contraction and relaxation; left ventricular end-diastolic pressure; myocardial oxygen consumption; and coronary flow reserve.

Symptoms of cardiac disorders, such as congestive heart failure, include chest pain, or angina; heart murmur or other abnormal sounds; fast or uneven pulse; an abnormal electrocardiogram or echocardiogram test; and an abnormal stress tests and electrocardiogram. Biomarkers of cardiac disorders, such as congestive heart failure, include: Brain Natriuretic Protein (BNP) and N-terminal fragments of the BNP propeptide (NT-ProBNP); troponins, particularly cardiac troponins (cTn), including troponin I and cardiac troponin I (cTnI); troponin T and cardiac troponin T (cTnT); troponin C (TnC); heart type fatty acid binding protein (hFABP); norepinephrine; atrial natriuretic peptide (ANP); galectin-3; C-reactive protein; tumor necrosis factor-α (TNF-α); interleukin-1; and interleukin-6.

In addition to each of the foregoing, the subject may also exhibit elevated levels of GDF15 activity relative to a baseline activity level present in subjects without the cardiac disorder or dysfunction.

Elevated levels of GDF15 activity can determined by measuring the level of GDF15 in a sample from a subject. The amount regarded as an "elevated level" of GDF15 may vary according to the particular tissue or body fluid of interest, as well as the particular assay that is utilized. Generally, an "elevated level" of GDF15 may be determined relative to a control distribution of subjects, for example, subjects without a cardiac disease or dysfunction, for example, CHF, and may be determined at a pre-specified cutoff of, for example, the $75^{th}$ percentile (i.e., upper quartile or 25%); $90^{th}$ percentile (i.e., upper 10%); or $95^{th}$ percentile (i.e., upper 5%). An "elevated level" of GDF15 may also be determined at a pre-specified GDF15 level above the mean, for example one standard deviation above the mean, or two standard deviations above the mean average GDF15 level of a group of control subjects without cardiac disease or dysfunction, for example, CHF. See, for example, Brown et al., 2002, The Lancet 359:2159-2163; Kempf et al., 2011, Nature Medicine, 17:581-588.

The preferred body sample is a body fluid, for example, a sample of blood plasma, however a sample of amniotic fluid, placental extract, whole blood, serum, buffy coat, urine, cerebrospinal fluid, seminal fluid, synovial fluid, or a tissue biopsy may also be suitable. A GDF15 concentration of >600 pg/ml, optionally >850 pg/ml, optionally >1000 pg/ml, optionally >1200 pg/ml, optionally >1500 pg/ml, optionally >1700 pg/ml, optionally >1900 pg/ml, optionally >2000 pg/ml, optionally >2500 pg/ml, and optionally >3000 pg/ml in a body fluid (e.g., plasma) can represent an elevated level of GDF15. See, U.S. Pat. No. 7,919,084 and Kempf et al., 2007, J. Am. Coll. Cardiol. 50:1054-1060.

The amount of GDF15 present in a body sample may be readily determined by, for example, immunoassays (e.g., with a body fluid) or immunohistochemistry (e.g., with sectionalized samples of a tissue biopsy) using an anti-GDF15 antibody. See Tsai et al., 2013, PLOS One, 8:e55174.

A subject is considered to be suffering from congestive heart failure if the subject's peak measurement of oxygen uptake (peak $VO_2$) is less than a normal value, e.g., 14 mL/kg/min. (See, Wilson et al., 1995, J. Am. Coll. Cardiol., 26:429-435; Lanier et al., 2012, J. Exercise Science & Fitness, 10:23-27). However, it is understood that "normal ranges" of peak $VO_2$ can vary depending upon the specific laboratory and test.

A subject is considered to be suffering from congestive heart failure if the subject's left ventricular ejection fraction (LVEF) is below a normal value, e.g., 40%. A subject whose LVEF is between 40 and 55% is considered to have below normal LVEF, and is considered to be at risk of CHF. LVEF can be measured, for example, using transthoracic echocardiography. (See, Cattadori et al., 2011, J. Cardiac Failure, 17:916-922). However, it is understood that "normal ranges" of LVEF can vary depending upon the specific laboratory and test.

A subject is considered to be suffering from congestive heart failure if the subject's serum BNP levels are in excess 100 pg/ml (mild CHF); or in excess of/below about 500 pg/ml (serious CHF). A subject is considered to be at risk of CHF if the subject's serum BNP levels are high normal or above normal ranges, at a level of 50 pg/ml or greater. The normal BNP range is considered to be at or below 50 pg/ml. "High normal" concentration is considered to be in the upper quarter (25%) of the normal range; preferably in the upper tenth (10%) of the normal range. See, for example, Strunk et al., 2006, Am. J. Med., 119:69e1-11; Clerico et al., 2012, Clin. Chim. Acta, 414:112-119. However, it is understood that "normal ranges" of BNP can vary depending upon the specific laboratory and test.

A subject is considered to be suffering from congestive heart failure if the subject's serum cardiac troponin I (cTnI) levels are in excess of 1.5 ng/mL (mild CHF), or in excess of 3.1 ng/mL (serious CHF). A subject is considered to be at risk of CHF if his or her serum troponin levels are high normal or above normal ranges, at a level of 1.5 ng/mL or greater. "High normal" concentration is considered to be in the upper quarter (25%) of the normal range; preferably in the upper tenth (10%) of the normal range. See, for example, Galvani et al., 1995, Circulation, 95:2053-2059. However, it is understood that "normal ranges" of troponin can vary depending upon the specific laboratory and test. Additionally, one skilled in the art will recognize that other tests are available for the diagnosis of chronic or congestive heart failure, based upon the quantitation of troponins, including other tests quantitating cTnI, overall TnI, overall cardiac troponins, troponin T (TnT), including high sensitivity TnT (hsTnT), troponin C and/or other troponins. See Heringlake et al., 2013, J. Am. Coll. Cardiol. 61:672-68.

In certain embodiments, a subject is considered to be suffering from congestive heart failure if the subject's performance in a test of exercise or physiological capacity is indicative of reduced peak $VO_2$, for example, in the six mile walking test (6MWT) or a shuttle walking test (SWT). See, Pulz et al., 2008, Canadian J. Cardiology, 24:131-135; Green et al., 2001, J. Science and Medicine in Sports 4:292-300. For example, a subject who covers a distance less than or equal to approximately 500 m in the 6MWT, or exhibits peak $VO_2$ of approximately 16.5 ml/kg or less during the 6MWT, is considered to be suffering from CHF. See Faggiano et al., 1997, American Heart Journal, 134:203-206. A subject who covers a distance less than or equal to approximately 450 m in the SWT, or exhibits peak $VO_2$ of less than approximately 14 ml/kg or less in the SWT is considered to be suffering from CHF. See, Morales et al., 1999, American Heart Journal, 138:291-298.

Typically, a subject is diagnosed to be suffering from congestive heart failure if the subject experiences pathological cardiac hypertrophy, or increase in heart mass, which is due to underlying disease. Pathological cardiac hypertrophy is frequently referred to as 'compensated cardiac hypertrophy,' because the heart muscle grows larger in response to a decrease in functionality of myocardial tissue. Pathological or compensated cardiac hypertrophy is different from physiological cardiac hypertrophy, or 'athlete's heart,' wherein a heart muscle grows larger in response to prolonged exercise and exercise regimens. Cardiac hypertrophy may be diagnosed using known techniques and indices. For example, left ventricular hypertrophy (LVH) can be diagnosed using echocardiography. The left ventricular myocardium is normally from about 0.6 to 1.1 cm in thickness at the end of diastole. If the myocardium is more than 1.1 cm thick, the diagnosis of LVH can be made. Cardiac hypertrophy can also result from dilated cardiomyopathy (DCM), wherein a portion of the myocardium may become dilated without apparent reason. DCM may be diagnosed by examination of chest x-rays, electrocardiogram or echocardiogram. (See, myclevelandclinic.org/heart/disorders/hcm/default.aspx.)

Similarly, a subject is considered to be suffering from congestive heart failure if the subject experiences or is diagnosed with pathological cardiac hypotrophy, or significant decrease in heart mass. Cardiac hypotrophy is often due to reduced left ventricular mass (LVM). Clinically, LVM is often observed in cases of anorexia nervosa, and can be diagnosed by echocardiogram. See Romano et al., 2003, Am. J. Clin. Nut., 77:308-313; Meczekalski et al., 2013, Maturitas, 75:215-220. It is understood that the methods and compositions of the invention can be useful in treating cardiac hypertrophy or cardiac hypotrophy as the methods and conditions ameliorate the symptoms of each condition to help restore normal heart structure, heart physiology, and/or cardiac function.

The above parameters can be easily measured before, during and after treatment with a GDF15 modulator.

In certain embodiments, treatment of a subject may improve the left ventricular ejection fraction by at least 1% (compared to the left ventricular ejection fraction prior to treatment). For example, treatment of a subject may improve the left ventricular ejection fraction by at least 2%, at least 3%, at least 4%, at least 5%, at least 6%, at least 7%, at least 8%, at least 9%, at least 10%, at least 12%, at least 14%, at least 16%, at least 18%, at least 20%, at least 25%, at least 30%, at least 35%, at least 40%, at least 45%, or at least 50%. The treatment may continue until the subject has attained a left ventricular ejection fraction of at least 30%, at least 31%, at least 32%, at least 33%, at least 34%, at least 35%, at least 36%, at least 37%, at least 38%, at least 39%, at least 40%, at least 41%, at least 42%, at least 43%, at least 44%, at least 45%, at least 46%, at least 47%, at least 48%, at least 49%, or at least 50%. The treatment may provide a residual improvement in the left ventricular ejection fraction for at least 5 minutes, at least 10 minutes, at least 20 minutes, at least 30 minutes, at least 45 minutes, at least 1 hour, at least 2 hours, at least 3 hours, at least 4 hours, at least 5 hours, at least 6 hours, at least 12 hours, at least 1 day, at least 2 days, at least 3 days, at least 4 days, at least 5 days, at least 6 days, at least 7 days, at least 10 days, at least 14 days, at least 21 days, or at least 28 days.

In certain embodiments, treatment of a subject may improve the cardiac output by at least 1% (compared to the cardiac output prior to treatment). For example, treatment of a subject may improve the cardiac output by at least 2%, at least 3%, at least 4%, at least 5%, at least 6%, at least 7%, at least 8%, at least 9%, at least 10%, at least 12%, at least 14%, at least 16%, at least 18%, at least 20%, at least 25%, at least 30%, at least 35%, at least 40%, at least 45%, or at least 50%. The treatment may continue until the subject has attained a cardiac output of at least 2.5 L/min, at least 3.0 L/min, at least 3.5 L/min, at least 4.0 L/min, at least 4.5 L/min, at least 5.0 L/min, or at least 5.25 L/min. The treatment may provide a residual improvement in the cardiac output for at least 5 minutes, at least 10 minutes, at least 20 minutes, at least 30 minutes, at least 45 minutes, at least 1 hour, at least 2 hours, at least 3 hours, at least 4 hours, at least 5 hours, at least 6 hours, at least 12 hours, at least 1 day, at least 2 days, at least 3 days, at least 4 days, at least 5 days, at least 6 days, at least 7 days, at least 10 days, at least 14 days, at least 21 days, or at least 28 days.

In certain embodiments, treatment of a subject may improve the left ventricular stroke volume by at least 1% (compared to the stroke volume prior to treatment). For example, treatment of a subject may improve the left ventricular stroke volume by at least 2%, at least 3%, at least 4%, at least 5%, at least 6%, at least 7%, at least 8%, at least 9%, at least 10%, at least 12%, at least 14%, at least 16%, at least 18%, at least 20%, at least 25%, at least 30%, at least 35%, at least 40%, at least 45%, or at least 50%. The treatment may continue until the subject has attained a left ventricular stroke volume of at least 27 ml, at least 30 ml, at least 35 ml, at least 40 ml, at least 45 ml, at least 50 ml, at least 55 ml, at least 60 ml, at least 65 ml, or at least 70 ml. The treatment may provide a residual improvement in left ventricular stroke volume for at least 5 minutes, at least 10 minutes, at least 20 minutes, at least 30 minutes, at least 45 minutes, at least 1 hour, at least 2 hours, at least 3 hours, at least 4 hours, at least 5 hours, at least 6 hours, at least 12 hours, at least 1 day, at least 2 days, at least 3 days, at least 4 days, at least 5 days, at least 6 days, at least 7 days, at least 10 days, at least 14 days, at least 21 days, or at least 28 days.

In certain embodiments, treatment of a subject may reduce the systemic vascular resistance by at least 1% (compared to the systemic vascular resistance prior to treatment). For example, treatment of a subject may reduce the systemic vascular resistance by at least 2%, at least 3%, at least 4%, at least 5%, at least 6%, at least 7%, at least 8%, at least 9%, at least 10%, at least 12%, at least 14%, at least 16%, at least 18%, at least 20%, at least 25%, at least 30%, at least 35%, at least 40%, at least 45%, or at least 50%. The treatment may continue until the subject has attained a systemic vascular resistance of no more than 3500 dyn·s/cm$^5$, no more than 3000 dyn·s/cm$^5$, no more than 2500 dyn·s/cm$^5$, no more than 2000 dyn·s/cm$^5$, or no more than 1600 dyn·s/cm$^5$. The treatment may provide a residual improvement in the systemic vascular resistance for at least 5 minutes, at least 10 minutes, at least 20 minutes, at least 30 minutes, at least 45 minutes, at least 1 hour, at least 2 hours, at least 3 hours, at least 4 hours, at least 5 hours, at least 6 hours, at least 12 hours, at least 1 day, at least 2 days, at least 3 days, at least 4 days, at least 5 days, at least 6 days, at least 7 days, at least 10 days, at least 14 days, at least 21 days, or at least 28 days.

II. Comorbidities of Chronic or Congestive Heart Failure

Chronic heart failure is frequently complicated by the occurrence of comorbidities, which may range from minor to serious in degree. It is an advantage of the present invention that inhibition of GDF15 may additionally assist in reducing one or more common comorbidities of CHF. Among the common comorbidities associated with CHF are cachexia, chronic kidney disease, anemia, iron deficiency and hypertension. Accordingly, the present invention includes methods of increasing cardiac function in a subject in need thereof, the method comprising administering an effective amount of a composition comprising a GDF15 inhibitor to increase cardiac function in a subject who exhibits one or more comorbidity of CHF. For example, the subject suffering from cardiac dysfunction or CHF may exhibit a comorbidity of cachexia, chronic kidney disease, anemia, iron deficiency or hypertension.

III. GDF15 Modulators

As used herein a "GDF15 modulator" is understood to mean an agent that reduces or inhibits GDF15 activity, which can result from reduced expression, amount, or biological activity or function, of GDF15. GDF15 modulators or modulating agents useful in the practice of the invention may comprise an anti-GDF15 antibody, an anti-GDF15 receptor antibody, soluble GDF15 mimetics or analogs that prevent GDF15 from binding to its cognate binding partner, a soluble GDF15 receptor mimetic or analog that prevents GDF15 from binding to its cognate binding partner. Additional exemplary GDF15 modulating agents include small molecule inhibitors of GDF15 or a GDF15 receptor, interfering nucleic acids (for example, interfering RNA or antisense nucleic acids (for example, antisense DNA or RNA) that interfere with expression of endogenous GDF15 or a cognate receptor.

In a preferred embodiment, the GDF15 modulating agent can comprise an anti-GDF15 antibody, which is humanized or human. As used herein, unless otherwise indicated, the term "antibody" is understood to mean an intact antibody (e.g., an intact monoclonal antibody) or antigen-binding fragment of an antibody, including an intact antibody or antigen-binding fragment of an antibody (e.g., a phage display antibody including a fully human antibody, a semisynthetic antibody or a fully synthetic antibody) that has been optimized, engineered or chemically conjugated. Examples of antibodies that have been optimized are affinity-matured antibodies. Examples of antibodies that have been engineered are Fc optimized antibodies, and multispecific antibodies (e.g., bispecific antibodies). Examples of antigen-binding fragments include Fab, Fab', $F(ab')_2$, Fv, single chain antibodies (e.g., scFv), minibodies and diabodies. An antibody conjugated to a toxin moiety is an example of a chemically conjugated antibody.

In certain embodiments, the antibody comprises: (a) an immunoglobulin heavy chain variable region comprising the structure $CDR_{H1}$-$CDR_{H2}$-$CDR_{H3}$ and (b) an immunoglobulin light chain variable region, wherein the heavy chain variable region and the light chain variable region together define a single binding site for binding GDF15 or a GDF15 receptor. The $CDR_{H1}$, $CDR_{H2}$, and $CDR_{H3}$ sequences are interposed between immunoglobulin framework (FR) sequences. In certain other embodiments, the antibody comprises (a) an immunoglobulin light chain variable region comprising the structure $CDR_{L1}$-$CDR_{L2}$-$CDR_{L3}$, and (b) an immunoglobulin heavy chain variable region, wherein the IgG light chain variable region and the IgG heavy chain variable region together define a single binding site for binding GDF15 or a GDF15 receptor. The $CDR_{L1}$, $CDR_{L2}$, and $CDR_{L3}$ sequences are interposed between immunoglobulin FR sequences. In certain other embodiments, the antibody comprises: (a) an immunoglobulin heavy chain variable region comprising the structure $CDR_{H1}$-$CDR_{H2}$-$CDR_{H3}$ and (b) an immunoglobulin light chain variable region comprising the structure $CDR_{L1}$-$CDR_{L2}$-$CDR_{L3}$, wherein the heavy chain variable region and the light chain variable region together define a single binding site for binding GDF15 or a GDF15 receptor. Exemplary anti-GDF15 antibodies are described, for example, in U.S. Patent Publication No. US 2014-0193427-A1, the disclosure of which is incorporated by reference herein for all purposes.

Exemplary anti-GDF15 antibodies useful in the methods and compositions of the invention may, for example, include a heavy chain variable region comprising any one of the nine sets of $CDR_{H1}$, $CDR_{H2}$, and $CDR_{H3}$ region sequences set forth in Table 1 below.

TABLE 1

| | $CDR_{H1}$ | $CDR_{H2}$ | $CDR_{H3}$ |
|---|---|---|---|
| 1 | DYNMD (SEQ ID NO: 1) | QINPNNGGIFFNQKFKG (SEQ ID NO: 4) | EAITTVGAMDY (SEQ ID NO: 13) |
| 2 | DYNMD (SEQ ID NO: 1) | QINPNNGGIFFNQKFQG (SEQ ID NO: 5) | EAITTVGAMDY (SEQ ID NO: 13) |
| 3 | DYNMD (SEQ ID NO: 1) | QINPYNHLIFFNQKFQG (SEQ ID NO: 6) | EAITTVGAMDY (SEQ ID NO: 13) |
| 4 | DYNMD (SEQ ID NO: 1) | QINPNNGLIFFNQKFQG (SEQ ID NO: 7) | EAITTVGAMDY (SEQ ID NO: 13) |
| 5 | DYNMD (SEQ ID NO: 1) | QINPNNGLIFFNQKFKG (SEQ ID NO: 8) | EAITTVGAMDY (SEQ ID NO: 13) |
| 6 | DYNMD (SEQ ID NO: 1) | QINPYNHLIFFNQKFKG (SEQ ID NO: 9) | EAITTVGAMDY (SEQ ID NO: 13) |
| 7 | TYGMGVS (SEQ ID NO: 2) | HIYWDDDKRYNPSLKS (SEQ ID NO: 10 | RGYDDYWGY (SEQ ID NO: 14) |
| 8 | TYGMGVS (SEQ ID NO: 2) | HIYWDDDKRYNPSLKT (SEQ ID NO: 11) | RGYDDYWGY (SEQ ID NO: 14) |
| 9 | TYGMGVG (SEQ ID NO: 3) | DIW-WDDDKYYNPSLKS (SEQ ID NO: 12) | RGHYSAMDY (SEQ ID NO: 15) |

Exemplary anti-GDF15 antibodies useful in the methods and compositions of the invention may, for example, include a light chain variable region comprising any one of the four sets of $CDR_{L1}$, $CDR_{L2}$, and $CDR_{L3}$ region sequences set forth in Table 2 below.

TABLE 2

| | $CDR_{L1}$ | $CDR_{L2}$ | $CDR_{L3}$ |
|---|---|---|---|
| 1 | RTSENLHNYLA (SEQ ID NO: 16) | DAKTLAD (SEQ ID NO: 18) | QHFWSSPYT (SEQ ID NO: 21) |
| 2 | RTSENLHNYLA (SEQ ID NO: 16) | DAKTLAD (SEQ ID NO: 18) | QHFWSDPYT (SEQ ID NO: 22) |
| 3 | KASQNVGTNVA (SEQ ID NO: 17) | SASYRYS (SEQ ID NO: 19) | QQYNNYPLT (SEQ ID NO: 23) |
| 4 | KASQNVGTNVA (SEQ ID NO: 17) | SPSYRYS (SEQ ID NO: 20) | QQYNSYPHT (SEQ ID NO: 24) |

Exemplary anti-GDF-15 antibodies useful in the practice of the invention are described in U.S. Patent Publication No. US 2014-0193427-A1, including 01G06, 03G05, 04F08, 06C11, 08G01, 14F11, 17B11, as well as human or humanized forms thereof. In certain embodiments, the antibodies disclosed herein (e.g., 01G06, 03G05, 04F08, 06C11, 08G01, 14F11, or 17B11, or humanized forms thereof) are used to treat CHF or another cardiac-related disease or disorder who exhibits symptoms of CHF or who is diagnosed as having CHF or at risk of having CHF. In some embodiments, the antibodies reverse a symptom or characteristic of CHF or another cardiac-related disease or disorder by at least 2%, 5%, 10%, 15%, 20%, 25%, 30% or 35%.

In a preferred embodiment, an anti-GDF-15 antibody useful in the practice of the invention is referred to as 01G06 in U.S. Patent Publication No. US 2014-0193427-A1. Humanized forms of the 01G06 antibody are listed below together with the amino acid sequences of their respective heavy and light chain variable regions. Exemplary humanized anti-GDF-15 antibodies include: Hu01G06-1; Hu01G06-46; Hu01G06-52; Hu01G06-100; Hu01G06-101; Hu01G06-102; Hu01G06-103; Hu01G06-104; Hu01G06-105; Hu01G06-106; Hu01G06-107; Hu01G06-108; Hu01G06-109; Hu01G06-110; Hu01G06-111; Hu01G06-112; Hu01G06-113; Hu01G06-114; Hu01G06-122; Hu01G06-127; Hu01G06-135; Hu01G06-138; Hu01G06-146; Hu06C11-1; Hu06C11-27; Hu06C11-30; Hu14F11-1; Hu14F11-23; Hu14F11-24; Hu14F11-39; and Hu14F11-47. The amino acid sequences for the heavy chain and light chain for each of the aforementioned antibodies is set forth below in Table 3.

TABLE 3

| Antibody Name | Light Chain | Heavy Chain |
|---|---|---|
| 01G06 (murine) | SEQ ID NO: 25 | SEQ ID NO: 37 |
| Hu01G06-1 | SEQ ID NO: 26 | SEQ ID NO: 38 |
| Hu01G06-46 | SEQ ID NO: 27 | SEQ ID NO: 39 |
| Hu01G06-52 | SEQ ID NO: 27 | SEQ ID NO: 40 |
| Hu01G06-100 | SEQ ID NO: 27 | SEQ ID NO: 41 |
| Hu01G06-101 | SEQ ID NO: 27 | SEQ ID NO: 42 |
| Hu01G06-102 | SEQ ID NO: 27 | SEQ ID NO: 43 |
| Hu01G06-103 | SEQ ID NO: 27 | SEQ ID NO: 44 |
| Hu01G06-104 | SEQ ID NO: 27 | SEQ ID NO: 45 |
| Hu01G06-105 | SEQ ID NO: 28 | SEQ ID NO: 41 |
| Hu01G06-106 | SEQ ID NO: 28 | SEQ ID NO: 42 |
| Hu01G06-107 | SEQ ID NO: 28 | SEQ ID NO: 43 |
| Hu01G06-108 | SEQ ID NO: 28 | SEQ ID NO: 44 |
| Hu01G06-109 | SEQ ID NO: 28 | SEQ ID NO: 45 |
| Hu01G06-110 | SEQ ID NO: 29 | SEQ ID NO: 41 |
| Hu01G06-111 | SEQ ID NO: 29 | SEQ ID NO: 42 |
| Hu01G06-112 | SEQ ID NO: 29 | SEQ ID NO: 43 |
| Hu01G06-113 | SEQ ID NO: 29 | SEQ ID NO: 44 |
| Hu01G06-114 | SEQ ID NO: 29 | SEQ ID NO: 45 |
| Hu01G06-122 | SEQ ID NO: 29 | SEQ ID NO: 46 |
| Hu01G06-127 | SEQ ID NO: 30 | SEQ ID NO: 47 |
| Hu01G06-135 | SEQ ID NO: 29 | SEQ ID NO: 48 |
| Hu01G06-138 | SEQ ID NO: 29 | SEQ ID NO: 49 |
| Hu01G06-146 | SEQ ID NO: 30 | SEQ ID NO: 49 |

TABLE 3-continued

| Antibody Name | Light Chain | Heavy Chain |
|---|---|---|
| 06C11 (murine) | SEQ ID NO: 31 | SEQ ID NO: 50 |
| Hu06C11-1 | SEQ ID NO: 32 | SEQ ID NO: 38 |
| Hu06C11-27 | SEQ ID NO: 33 | SEQ ID NO: 51 |
| Hu06C11-30 | SEQ ID NO: 33 | SEQ ID NO: 52 |
| 14F11 (murine) | SEQ ID NO: 34 | SEQ ID NO: 53 |
| Hu14F11-1 | SEQ ID NO: 35 | SEQ ID NO: 54 |
| Hu14F11-23 | SEQ ID NO: 35 | SEQ ID NO: 55 |
| Hu14F11-24 | SEQ ID NO: 32 | SEQ ID NO: 54 |
| Hu14F11-39 | SEQ ID NO: 36 | SEQ ID NO: 56 |
| Hu14F11-47 | SEQ ID NO: 36 | SEQ ID NO: 57 |

It is understood that the antibodies described herein can be designed, tested, and formulated using techniques known in the art.

```
                                                        SEQ ID NO: 25
  1 diqmtqspas lsasvgetvt itcrtsenlh nylawyqqkq gkspqllvyd aktladgvps

 61 rfsgsgsgtq yslkinslqp edfgsyycqh fwsspytfgg gtkleikrad aaptvsifpp

121 sseqltsgga svvcflnnfy pkdinvkwki dgserqngvl nswtdqdskd stysmsstlt

181 ltkdeyerhn sytceathkt stspivksfn rnec

                                                        SEQ ID NO: 26
  1 diqmtqspas lsasvgetvt itcrtsenlh nylawyqqkq gkspqllvyd aktladgvps

 61 rfsgsgsgtq yslkinslqp edfgsyycqh fwsspytfgg gtkleikrtv aapsvfifpp

121 sdeqlksgta svvcllnnfy preakvqwkv dnalqsgnsq esvteqdskd styslsstlt

181 lskadyekhk vyacevthqg lsspvtksfn rgec

                                                        SEQ ID NO: 27
  1 diqmtqspss lsasvgdrvt itcrtsenlh nylawyqqkp gkspkllvyd aktladgvps

 61 rfsgsgsgtd ytltisslqp edfatyycqh fwsspytfgq gtkleikrtv aapsvfifpp

121 sdeqlksgta svvcllnnfy preakvqwkv dnalqsgnsq esvteqdskd styslsstlt

181 lskadyekhk vyacevthqg lsspvtksfn rgec

                                                      []SEQ ID NO: 29
  1 diqmtqspss lsasvgdrvt itcrtsenlh nylawyqqkp gkapklliyd aktladgvps

 61 rfsgsgsgtd ytltisslqp edfatyycqh fwsspytfgq gtkleikrtv aapsvfifpp

121 sdeqlksgta svvcllnnfy preakvqwkv dnalqsgnsq esvteqdskd styslsstlt

181 lskadyekhk vyacevthqg lsspvtksfn rgec

                                                        SEQ ID NO: 28
  1 diqmtqspss lsasvgdrvt itcrtsenlh nylawyqqkp gkspklliyd aktladgvps

 61 rfsgsgsgtd ytltisslqp edfatyycqh fwsspytfgq gtkleikrtv aapsvfifpp

121 sdeqlksgta svvcllnnfy preakvqwkv dnalqsgnsq esvteqdskd styslsstlt

181 lskadyekhk vyacevthqg lsspvtksfn rgec

                                                      []SEQ ID NO: 32
  1 divmtqsqkf mstsvgdrvs vtckasqnvg tnvawfqqkp gqspkaliys asyrysgvpd

 61 rftgsgsgtd filtisnvqs edlaeyfcqq ynnypltfga gtkleikrtv aapsvfifpp

121 sdeqlksgta svvcllnnfy preakvqwkv dnalqsgnsq esvteqdskd styslsstlt

181 lskadyekhk vyacevthqg lsspvtksfn rgec

                                                        SEQ ID NO: 33
  1 diqmtqspss lsasvgdrvt itckasqnvg tnvawfqqkp gkapksliys asyrysgvps

 61 rfsgsgsgtd ftltisslqp edfatyycqq ynnypltfgq gtkleikrtv aapsvfifpp

121 sdeqlksgta svvcllnnfy preakvqwkv dnalqsgnsq esvteqdskd styslsstlt

181 lskadyekhk vyacevthqg lsspvtksfn rgec

                                                      []SEQ ID NO: 35
  1 divmtqsqkf mstsvgdrvs vtckasqnvg tnvawyqqkp gqspkaliys psyrysgvpd

 61 rftgsgsgtd ftltisnvqs edlaeyfcqq ynsyphtfgg gtklemkrtv aapsvfifpp
```

-continued

```
121 sdeqlksgta svvcllnnfy preakvqwkv dnalqsgnsq esvteqdskd styslsstlt

181 iskadyekhk vyacevthqg lsspvtksfn rgec

                                                  []SEQ ID NO: 36
  1 diqmtqspss lsasvgdrvt itckasqnvg tnvawfqqkp gkspkaliys psyrysgvps

 61 rfsgsgsgtd ftltisslqp edfatyfcqq ynsyphtfgg gtkleikrtv aapsvfifpp

121 sdeqlksgta svvcllnnfy preakvqwkv dnalqsgnsq esvteqdskd styslsstlt

181 lskadyekhk vyacevthqg lsspvtksfn rgec

                                                  []SEQ ID NO: 37
  1 evllqqsgpe lvkpgasvki pckasgytft dynmdwvkgs hgkslewigq inpnnggiff

 61 nqkfkgkatl tvdkssntaf mevrsitsed tavyycarea ittvgamdyw gqgtsvtvss

121 akttppsvyp lapgsaaqtn smvtlgclvk gyfpepvtvt wnsgslssgv htfpavlgsd

181 lytlsssvtv psstwpsetv tcnvahpass tkvdkkivpr dcgckpcict vpevssvfif

241 ppkpkdvlti tltpkvtcvv vdiskddpev gfswfvddve vhtagtgpre egfnstfrsv

301 selpimhqdw ingkefkcrv nsaafpapie ktisktkgrp kapgvytipp pkeqmakdkv

361 sltcmitdff peditvewqw ngqpaenykn tgpimdtdgs yfvysklnvg ksnweagntf

421 tcsvlheglh nhhtekslsh spgk

                                                  []SEQ ID NO: 30
  1 diqmtqspss lsasvgdrvt itcrtsenlh nylawyggkp gkspklliyd aktladgvps

 61 rfsgsgsgtd ytltisslqp edfatyycqh fwsdpytfgg gtkleikrtv aapsvfifpp

121 sdeqlksgta svvcllnnfy preakvqwkv dnalqsgnsq esvteqdskd styslsstlt

181 lskadyekhk vyacevthqg lsspvtksfn rgec

                                                    SEQ ID NO: 38
  1 evllqqsgpe lvkpgasvki pckasgytft dynmdwvkqs hgkslewigq inpnnggiff

 61 nqkfkgkatl tvdkssntaf mevrsitsed tavyycarea ittvgamdyw gqgtsvtvss

121 astkgpsvfp lapsskstsg gtaalgclvk dyfpepvtvs wnsgaltsgv htfpavlgss

181 glyslssvvt vpssslgtqt yicnvnhkps ntkvdkrvep kscdkthtcp pcpapellgg

241 psvfifppkp kdtlmisrtp evtcvvvdvs hedpevkfnw yvdgvevhna ktkpreegyn

301 styrvvsvlt vlhqdwlngk eykckvsnka lpapiektis kakggprepg vytippsree

361 mtknqvsltc ivkgfypsdi avewesngqp ennykttppv ldsdgsffly skltvdksrw

421 qqgnvfscsv mhealhnhyt qkslslspgk

                                                  []SEQ ID NO: 39
  1 qvqlvqsgae vkkpgasvkv sckasgytft dynmdwvrga pgkslewigq inpnnggiff

 61 nqkfkgratl tvdtstntay melrslrsdd tavyycarea ittvgamdyw gggtlvtvss

121 astkgpsvfp lapsskstsg gtaalgclvk dyfpepvtvs wnsgaltsgv htfpavlqss

181 glyslssvvt vpssslgtqt yicnvnhkps ntkvdkrvep kscdkthtcp pcpapellgg

241 psvfifppkp kdtlmisrtp evtcvvvdvs hedpevkfnw yvdgvevhna ktkpreeqyn

301 styrvvsvlt vlhqdwlngk eykckvsnka lpapiektis kakgqprepq vytippsree

361 mtknqvsltc lvkgfypsdi avewesngqp ennykttppv ldsdgsffly skltvdksrw

421 qqgnvfscsv mhealhnhyt qkslslspgk

                                                  []SEQ ID NO: 40
  1 qvqlvqsgae vkkpgssvkv sckasgytft dynmdwvrqa pgkslewigq inpnnggiff

 61 nqkfkgratl tvdkstntay melsslrsed tavyycarea ittvgamdyw gqgtlvtvss

121 astkgpsvfp lapsskstsg gtaalgclvk dyfpepvtvs wnsgaltsgv htfpavlqss
```

-continued 181 glyslssvvt vpssslgtqt yicnvnhkps ntkvdkrvep kscdkthtcp pcpapellgg 241 psvflfppkp kdtlmisrtp evtcvvvdvs hedpevkfnw yvdgvevhna ktkpreeqyn 301 styrvvsvlt vlhqdwlngk eykckvsnka lpapiektis kakgqprepq vytippsree 361 mtknqvsltc lvkgfypsdi avewesngqp ennykttppv ldsdgsffly skltvdksrw 421 qqgnvfscsv mhealhnhyt qkslslspgk

[]SEQ ID NO: 41

1 qvqlvqsgae vkkpgasvkv sckasgytft dynmdwvrqa pgqglewmgq inpnnggiff 61 nqkfkgrvtl ttdtststay melrsirsdd tavyycarea ittvgamdyw gqgtlvtvss 121 astkgpsvfp lapsskstsg gtaalgclvk dyfpepvtvs wnsgaltsgv htfpavlqss 181 glyslssvvt vpssslgtqt yicnvnhkps ntkvdkrvep kscdkthtcp pcpapellgg 241 psvflfppkp kdtlmisrtp evtcvvvdvs hedpevkfnw yvdgvevhna ktkpreeqyn 301 styrvvsvlt vlhqdwlngk eykckvsnka lpapiektis kakgqprepq vytippsree 361 mtknqvsltc lvkgfypsdi avewesngqp ennykttppv ldsdgsffly skltvdksrw 421 qqgnvfscsv mhealhnhyt qkslslspgk

[SEQ ID NO: 43

1 qvqlvqsgae vkkpgasvkv sckasgytft dynmdwvrqa pgqslewmgq inpnnggiff 61 nqkfqgrvtl ttdtststay melrsirsdd tavyycarea ittvgamdyw gqgtlvtvss 121 astkgpsvfp lapsskstsg gtaalgclvk dyfpepvtvs wnsgaltsgv htfpavlqss 181 glyslssvvt vpssslgtqt yicnvnhkps ntkvdkrvep kscdkthtcp pcpapellgg 241 psvflfppkp kdtlmisrtp evtcvvvdvs hedpevkfnw yvdgvevhna ktkpreeqyn 301 styrvvsvlt vlhqdwlngk eykckvsnka lpapiektis kakgqprepq vytippsree 361 mtknqvsltc lvkgfypsdi avewesngqp ennykttppv ldsdgsffly skltvdksrw 421 qqgnvfscsv mhealhnhyt qkslslspgk

SEQ ID NO: 42

1 qvqlvqsgae vkkpgasvkv sckasgytft dynmdwvrqa pgqglewmgq inpnnggiff 61 nqkfqgrvtl ttdtststay melrsirsdd tavyycarea ittvgamdyw gqgtlvtvss 121 astkgpsvfp lapsskstsg gtaalgclvk dyfpepvtvs wnsgaltsgv htfpavlqss 181 glyslssvvt vpssslgtqt yicnvnhkps ntkvdkrvep kscdkthtcp pcpapellgg 241 psvflfppkp kdtlmisrtp evtcvvvdvs hedpevkfnw yvdgvevhna ktkpreeqyn 301 styrvvsvlt vlhqdwlngk eykckvsnka lpapiektis kakgqprepq vytippsree 361 mtknqvsltc lvkgfypsdi avewesngqp ennykttppv ldsdgsffly skltvdksrw 421 qqgnvfscsv mhealhnhyt qkslslspgk

SEQ ID NO: 44

1 qvqlvqsgae vkkpgssvkv sckasgytfs dynmdwvrqa pgqglewmgq inpnnggiff 61 nqkfkgrvtl tadkststay melsslrsed tavyycarea ittvgamdyw gqgtlvtvss 121 astkgpsvfp lapsskstsg gtaalgclvk dyfpepvtvs wnsgaltsgv htfpavlqss 181 glyslssvvt vpssslgtqt yicnvnhkps ntkvdkrvep kscdkthtcp pcpapellgg 241 psvfifppkp kdtlmisrtp evtcvvvdvs hedpevkfnw yvdgvevhna ktkpreeqyn 301 styrvvsvlt vlhqdwlngk eykckvsnka lpapiektis kakgqprepq vytlppsree 361 mtknqvsltc lvkgfypsdi avewesngqp ennykttppv ldsdgsffly skltvdksrw 421 qqgnvfscsv mhealhnhyt qkslslspgk

SEQ ID NO: 45

1 qvqlvqsgae vkkpgssvkv sckasgytfs dynmdwvrqa pgqglewmgq inpnnggiff

-continued 61 nqkfqgrvtl tadkststay melsslrsed tavyycarea ittvgamdyw gqgtlvtvss 121 astkgpsvfp lapsskstsg gtaalgclvk dyfpepvtvs wnsgaltsgv htfpavlqss 181 glyslssvvt vpssslgtqt yicnvnhkps ntkvdkrvep kscdkthtcp pcpapellgg 241 psvfifppkp kdtlmisrtp evtcvvvdvs hedpevkfnw yvdgvevhna ktkpreeqyn 301 styrvvsvlt vlhqdwlngk eykckvsnka lpapiektis kakgqprepq vytlppsree 361 mtknqvsltc lvkgfypsdi avewesngqp ennykttppv ldsdgsffly skltvdksrw 421 qqgnvfscsv mhealhnhyt qkslslspgk

SEQ ID NO: 46

1 qvqlvqsgae vkkpgasvkv sckasgytft dynmdwvrqa pgqslewmgq inpynhliff 61 nqkfqgrvtl ttdtststay melrslrsdd tavyycarea ittvgamdyw gqgtlvtvss 121 astkgpsvfp lapsskstsg gtaalgclvk dyfpepvtvs wnsgaltsgv htfpavlqss 181 glyslssvvt vpssslgtqt yicnvnhkps ntkvdkrvep kscdkthtcp pcpapellgg 241 psvfifppkp kdtlmisrtp evtcvvvdvs hedpevkfnw yvdgvevhna ktkpreeqyn 301 styrvvsvlt vlhqdwlngk eykckvsnka lpapiektis kakgqprepq vytlppsree 361 mtknqvsltc lvkgfypsdi avewesngqp ennykttppv ldsdgsffly skltvdksrw 421 qqgnvfscsv mhealhnhyt qkslslspgk

SEQ ID NO: 47

1 qvqlvqsgae vkkpgasvkv sckasgytft dynmdwvrqa pgqslewmgq inpnngliff 61 nqkfqgrvtl ttdtststay melrslrsdd tavyycarea ittvgamdyw gqgtlvtvss 121 astkgpsvfp lapsskstsg gtaalgclvk dyfpepvtvs wnsgaltsgv htfpavlqss 181 glyslssvvt vpssslgtqt yicnvnhkps ntkvdkrvep kscdkthtcp pcpapellgg 241 psvfifppkp kdtlmisrtp evtcvvvdvs hedpevkfnw yvdgvevhna ktkpreeqyn 301 styrvvsvlt vlhqdwlngk eykckvsnka lpapiektis kakgqprepq vytlppsree 361 mtknqvsltc lvkgfypsdi avewesngqp ennykttppv ldsdgsffly skltvdksrw 421 qqgnvfscsv mhealhnhyt qkslslspgk

SEQ ID NO: 48

1 qvqlvqsgae vkkpgssvkv sckasgytfs dynmdwvrqa pgqglewmgq inpnngliff 61 nqkfkgrvtl tadkststay melsslrsed tavyycarea ittvgamdyw gqgtlvtvss 121 astkgpsvfp lapsskstsg gtaalgclvk dyfpepvtvs wnsgaltsgv htfpavlqss 181 glyslssvvt vpssslgtqt yicnvnhkps ntkvdkrvep kscdkthtcp pcpapellgg 241 psvfifppkp kdtlmisrtp evtcvvvdvs hedpevkfnw yvdgvevhna ktkpreeqyn 301 styrvvsvlt vlhqdwlngk eykckvsnka lpapiektis kakgqprepq vytlppsree 361 mtknqvsltc lvkgfypsdi avewesngqp ennykttppv ldsdgsffly skltvdksrw 421 qqgnvfscsv mhealhnhyt qkslslspgk

SEQ ID NO: 49

1 qvqlvqsgae vkkpgssvkv sckasgytfs dynmdwvrqa pgqglewmgq inpynhliff 61 nqkfkgrvtl tadkststay melsslrsed tavyycarea ittvgamdyw gqgtlvtvss 121 astkgpsvfp lapsskstsg gtaalgclvk dyfpepvtvs wnsgaltsgv htfpavlqss 181 glyslssvvt vpssslgtqt yicnvnhkps ntkvdkrvep kscdkthtcp pcpapellgg 241 psvflfppkp kdtlmisrtp evtcvvvdvs hedpevkfnw yvdgvevhna ktkpreeqyn 301 styrvvsvlt vlhqdwlngk eykckvsnka lpapiektis kakgqprepq vytippsree 361 mtknqvsltc lvkgfypsdi avewesngqp ennykttppv ldsdgsffly skltvdksrw 421 qqgnvfscsv mhealhnhyt qkslslspgk -continued

SEQ ID NO: 38

```
  1 evllqqsgpe ivkpgasvki pckasgytft dynmdwvkqs hgkslewigq inpnnggiff
 61 nqkfkgkatl tvdkssntaf mevrsitsed tavyycarea ittvgamdyw gqgtsvtvss
121 astkgpsvfp lapsskstsg gtaalgclvk dyfpepvtvs wnsgaltsgv htfpavlqss
181 glyslssvvt vpssslgtqt yicnvnhkps ntkvdkrvep kscdkthtcp pcpapellgg
241 psvflfppkp kdtlmisrtp evtcvvvdvs hedpevkfnw yvdgvevhna ktkpreeqyn
301 styrvvsvlt vlhqdwlngk eykckvsnka lpapiektis kakgqprepq vytippsree
361 mtknqvsltc lvkgfypsdi avewesngqp ennykttppv ldsdgsffly skltvdksrw
421 qqgnvfscsv mhealhnhyt qkslslspgk
```

SEQ ID NO: 51

```
  1 qvtlkesgpa lvkptqtltl tctfsgfsin tygmgvswir qppgkalewl ahiywdddkr
 61 ynpslktrlt iskdtsknqv vltitnvdpv dtavyycaqr gyddywgywg qgtlvtissa
121 stkgpsvfpl apsskstsgg taalgclvkd yfpepvtvsw nsgaltsgvh tfpavlqssg
181 lyslssvvtv pssslgtqty icnvnhkpsn tkvdkrvepk scdkthtcpp cpapellggp
241 svfifppkpk dtlmisrtpe vtcvvvdvsh edpevkfnwy vdgvevhnak tkpreeqyns
301 tyrvvsvltv lhqdwlngke ykckvsnkal papiektisk akgqprepqv ytippsreem
361 tknqvsltcl vkgfypsdia vewesngqpe nnykttppvl dsdgsfflys kltvdksrwq
421 qgnvfscsvm healhnhytq kslslspgk
```

SEQ ID NO: 52

```
  1 qvtlkesgpt lvkptqtltl tctfsgfsin tygmgvswir qppgkglewl ahiywdddkr
 61 ynpslksrlt itkdtsknqv vltitnmdpv dtatyycaqr gyddywgywg qgtlvtvssa
121 stkgpsvfpl apsskstsgg taalgclvkd yfpepvtvsw nsgaltsgvh tfpavlqssg
181 lyslssvvtv pssslgtqty icnvnhkpsn tkvdkrvepk scdkthtcpp cpapellggp
241 svfifppkpk dtlmisrtpe vtcvvvdvsh edpevkfnwy vdgvevhnak tkpreeqyns
301 tyrvvsvltv lhqdwlngke ykckvsnkal papiektisk akgqprepqv ytippsreem
361 tknqvsltcl vkgfypsdia vewesngqpe nnykttppvl dsdgsfflys kltvdksrwq
421 qgnvfscsvm healhnhytq kslslspgk
```

SEQ ID NO: 54

```
  1 qvtlkesgpg ilqpsqtlsl tcsfsgfsis tygmgvgwir qpsgkglewl adiwwdddky
 61 ynpslksrlt iskdtssnev fIkiaivdta dtatyycarr ghysamdywg qgtsvtvssa
121 stkgpsvfpl apsskstsgg taalgclvkd yfpepvtvsw nsgaltsgvh tfpavlqssg
181 lyslssvvtv pssslgtqty icnvnhkpsn tkvdkrvepk scdkthtcpp cpapellggp
241 svfifppkpk dtlmisrtpe vtcvvvdvsh edpevkfnwy vdgvevhnak tkpreeqyns
301 tyrvvsvltv lhqdwlngke ykckvsnkal papiektisk akgqprepqv ytippsreem
361 tknqvsltcl vkgfypsdia vewesngqpe nnykttppvl dsdgsfflys kltvdksrwq
421 qgnvfscsvm healhnhytq kslslspgk
```

SEQ ID NO: 55

```
  1 qvtlkesgpg ilqpsqtlsl tcsfsgfsin tygmgvswir qpsgkglewl ahiywdddkr
 61 ynpslksrlt iskdasnnrv fikitsvdta dtatyycaqr gyddywgywg qgtlvtisaa
121 stkgpsvfpl apsskstsgg taalgclvkd yfpepvtvsw nsgaltsgvh tfpavlqssg
181 lyslssvvtv pssslgtqty icnvnhkpsn tkvdkrvepk scdkthtcpp cpapellggp
241 svfifppkpk dtlmisrtpe vtcvvvdvsh edpevkfnwy vdgvevhnak tkpreeqyns
301 tyrvvsvltv lhqdwlngke ykckvsnkal papiektisk akgqprepqv ytippsreem
```

-continued 361 tknqvsltcl vkgfypsdia vewesngqpe nnykttppvl dsdgsfflys kltvdksrwq 421 qgnvfscsvm healhnhytq kslslspgk

[SEQ ID NO: 56

1 qitlkesgpt lvkptqtltl tctfsgfsis tygmgvgwir qppgkalewl adiwwdddky 61 ynpslksrlt itkdtsknqv vltmtnmdpv dtatyycarr ghysamdywg qgtlvtvssa 121 stkgpsvfpl apsskstsgg taalgclvkd yfpepvtvsw nsgaltsgvh tfpavlqssg 181 lyslssvvtv pssslgtqty icnvnhkpsn tkvdkrvepk scdkthtcpp cpapellggp 241 svfifppkpk dtlmisrtpe vtcvvvdvsh edpevkfnwy vdgvevhnak tkpreeqyns 301 tyrvvsvltv lhqdwlngke ykckvsnkal papiektisk akgqprepqv ytippsreem 361 tknqvsltcl vkgfypsdia vewesngqpe nnykttppvl dsdgsfflys kltvdksrwq 421 nvfscsvm healhnhytq kslslspgk

[SEQ ID NO: 57

1 qvtlkesgpa lvkptqtltl tctfsgfsis tygmgvgwir qppgkalewl adiwwdddky 61 ynpslksrlt iskdtsknqv vltmtnmdpv dtavyycarr ghysamdywg qgtlvtvssa 121 stkgpsvfpl apsskstsgg taalgclvkd yfpepvtvsw nsgaltsgvh tfpavlqssg 181 lyslssvvtv pssslgtqty icnvnhkpsn tkvdkrvepk scdkthtcpp cpapellggp 241 svfifppkpk dtlmisrtpe vtcvvvdvsh edpevkfnwy vdgvevhnak tkpreeqyns 301 tyrvvsvltv lhqdwlngke ykckvsnkal papiektisk akgqprepqv ytippsreem 361 tknqvsltcl vkgfypsdia vewesngqpe nnykttppvl dsdgsfflys kltvdksrwq 421 qgnvfscsvm healhnhytq kslslspgk

[SEQ ID NO: 50

1 qvtlkesgpg ilqpsqtlsl tcsfsgfsin tygmgvswir qpsgkglewl ahiywdddkr 61 ynpslksrlt iskdasnnrv fIkitsvdta dtatyycaqr gyddywgywg qgtlvtisaa 121 kttppsvypl apgsaaqtns mvtlgclvkg yfpepvtvtw nsgslssgvh tfpavlqsdl 181 ytlsssvtvp sstwpsetvt cnvahpasst kvdkkivprd cgckpcictv pevssvfifp 241 pkpkdvitit ltpkvtcvvv diskddpevq fswfvddvev htaqtqpree qfnstfrsvs 301 elpimhqdwl ngkefkcrvn saafpapiek tisktkgrpk apqvytippp keqmakdkvs 361 ltcmitdffp editvewqwn gqpaenyknt qpimdtdgsy fvysklnvqk snweagntft 421 csvlheglhn hhtekslshs pgk

SEQ ID NO: 31

1 divmtqsqkf mstsvgdrvs vtckasqnvg tnvawfqqkp gqspkaliys asyrysgvpd 61 rftgsgsgtd filtisnvqs edlaeyfcqq ynnypltfga gtklelkrad aaptvsifpp 121 sseqltsgga svvcflnnfy pkdinvkwki dgserqngvl nswtdqdskd stysmsstlt 181 ltkdeyerhn sytceathkt stspivksfn

SEQ ID NO: 53

1 qvtlkesgpg ilqpsqtlsl testsgfsis tygmgvgwir qpsgkglewl adiwwdddky 61 ynpslksrlt iskdtssnev fikiaivdta dtatyycarr ghysamdywg qgtsvtvssa 121 kttppsvypl apgsaaqtns mvtlgclvkg yfpepvtvtw nsgslssgvh tfpavlqsdl 181 ytlsssvtvp sstwpsetvt envahpasst kvdkkivprd cgckpcictv pevssvfifp 241 pkpkdvltit ltpkvtcvvv diskddpevq fswfvddvev htaqtqpree qfnstfrsvs 301 elpimhqdwl ngkefkcrvn saafpapiek tisktkgrpk apqvytippp keqmakdkvs 361 ltcmitdffp editvewqwn gqpaenyknt qpimdtdgsy fvysklnvqk snweagntft 421 csvlheglhn hhtekslshs pgk -continued

SEQ ID NO: 34

```
  1 divmtqsqkf mstsvgdrvs vtckasqnvg tnvawyqqkp gqspkaliys psyrysgvpd

 61 rftgsgsgtd ftltisnvqs edlaeyfcqq ynsyphtfgg gtklemkrad aaptvsifpp

121 sseqltsgga svvcflnnfy pkdinvkwki dgserqngvl nswtdqdskd stysmsstlt

181 ltkdeyerhn sytceathkt stspivksfn rnec
```

The antibody may be a neutralizing antibody, which reduces GDF15 activity. For example, the antibody may reduce GDF15 activity in an in vivo assay (see, e.g., Johnen et al., 2007, Nature Medicine 13:1333-1340) by at least 10%, preferably 20%, 30% or 40%, and more preferably at least about 50%, 60%, 80% or 90% of GDF15 compared to GDF15 activity measured in the same assay under the same conditions in the absence of the antibody. The antibody may selectively and/or significantly reduce or inhibit the binding of GDF15 to its endogenous receptor. As used herein, the term "significantly reduces or inhibits binding" of GDF15 to its receptor is understood to mean that the antibody inhibits GDF15 binding with a potency or percent inhibition that measures at least 10%, preferably 20%, 30% or 40%, and more preferably at least about 50%, 60%, 80% or 90% of GDF15 (serum level/activity) in the absence of said antibody. Binding can be measured using a direct or sandwich enzyme-linked immunosorbent assay (ELISA), as described, e.g., in Tsai et al., 2013, PLOS One, 8:e55174. As used herein, the term "selectively" in the context of an antibody that binds to GDF15 or GDF15 receptor is understood to mean that the antibody binds GDF15 or a GDF15 receptor with a binding affinity that is at least two, three, four, five or ten times greater than that of a functionally unrelated protein or another member of the TGF-β superfamily or a receptor of a member of the TGF-β superfamily.

Methods for reducing or eliminating the antigenicity of antibodies and antibody fragments are known in the art. When the antibodies are to be administered to a human, the antibodies preferably are "humanized" to reduce or eliminate antigenicity in humans. Preferably, each humanized antibody has the same or substantially the same affinity for the antigen as the non-humanized mouse antibody from which it was derived.

In one humanization approach, chimeric proteins are created in which mouse immunoglobulin constant regions are replaced with human immunoglobulin constant regions. See, e.g., Morrison et al., 1984, Proc. Nat. Acad. Sci. 81:6851-6855, Neuberger et al., 1984, Nature 312:604-608; U.S. Pat. No. 6,893,625 (Robinson); U.S. Pat. No. 5,500,362 (Robinson); and U.S. Pat. No. 4,816,567 (Cabilly).

In an approach known as CDR grafting, the CDRs of the light and heavy chain variable regions are grafted into frameworks from another species. For example, murine CDRs can be grafted into human FRs. In some embodiments, the CDRs of the light and heavy chain variable regions of an anti-GDF15 antibody are grafted into human FRs or consensus human FRs. To create consensus human FRs, FRs from several human heavy chain or light chain amino acid sequences are aligned to identify a consensus amino acid sequence. CDR grafting is described in U.S. Pat. No. 7,022,500 (Queen); U.S. Pat. No. 6,982,321 (Winter); U.S. Pat. No. 6,180,370 (Queen); U.S. Pat. No. 6,054,297 (Carter); U.S. Pat. No. 5,693,762 (Queen); U.S. Pat. No. 5,859,205 (Adair); U.S. Pat. No. 5,693,761 (Queen); U.S. Pat. No. 5,565,332 (Hoogenboom); U.S. Pat. No. 5,585,089 (Queen); U.S. Pat. No. 5,530,101 (Queen); Jones et al., 1986, Nature 321: 522-525; Riechmann et al., 1988, Nature 332: 323-327; Verhoeyen et al., 1988, Science 239: 1534-1536; and Winter, 1998, FEBS Lett 430: 92-94.

In an approach called "SUPERHUMANIZATION™," human CDR sequences are chosen from human germline genes, based on the structural similarity of the human CDRs to those of the mouse antibody to be humanized. See, e.g., U.S. Pat. No. 6,881,557 (Foote); and Tan et al., 2002, J. Immunol. 169:1119-1125.

Other methods to reduce immunogenicity include "reshaping," "hyperchimerization," and "veneering/resurfacing." See, e.g., Vaswami et al., 1998, Annals of Allergy, Asthma, & Immunol. 81:105; Roguska et al., 1996, Prot. Engineer 9:895-904; and U.S. Pat. No. 6,072,035 (Hardman). In the veneering/resurfacing approach, the surface accessible amino acid residues in the murine antibody are replaced by amino acid residues more frequently found at the same positions in a human antibody. This type of antibody resurfacing is described, e.g., in U.S. Pat. No. 5,639,641 (Pedersen).

Another approach for converting a mouse antibody into a form suitable for medical use in humans is known as ACTIVMAB™ technology (Vaccinex, Inc., Rochester, NY), which involves a vaccinia virus-based vector to express antibodies in mammalian cells. High levels of combinatorial diversity of IgG heavy and light chains are said to be produced. See, e.g., U.S. Pat. No. 6,706,477 (Zauderer); U.S. Pat. No. 6,800,442 (Zauderer); and U.S. Pat. No. 6,872,518 (Zauderer).

Another approach for converting a mouse antibody into a form suitable for use in humans is technology practiced commercially by KaloBios Pharmaceuticals, Inc. (Palo Alto, CA). This technology involves the use of a proprietary human "acceptor" library to produce an "epitope focused" library for antibody selection.

Another approach for modifying a mouse antibody into a form suitable for medical use in humans is HUMAN ENGINEERING™ technology, which is practiced commercially by XOMA (US) LLC. See, e.g., PCT Publication No. WO 93/11794 and U.S. Pat. No. 5,766,886 (Studnicka); U.S. Pat. No. 5,770,196 (Studnicka); U.S. Pat. No. 5,821,123 (Studnicka); and U.S. Pat. No. 5,869,619 (Studnicka).

Any suitable approach, including any of the above approaches, can be used to reduce or eliminate human immunogenicity of an antibody.

In addition, it is possible to create fully human antibodies in mice. Fully human mAbs lacking any non-human sequences can be prepared from human immunoglobulin transgenic mice by techniques referenced in, e.g., Lonberg et al., Nature 368:856-859, 1994; Fishwild et al., Nature Biotechnology 14:845-851, 1996; and Mendez et al., Nature Genetics 15:146-156, 1997. Fully human mAbs can also be prepared and optimized from phage display libraries by techniques referenced in, e.g., Knappik et al., J. Mol. Biol. 296:57-86, 2000; and Krebs et al., J. Immunol. Meth. 254: 67-84 2001).

It is contemplated that variants and derivatives of GDF15 that act as decoys can be useful in the practice of the invention. For example, through deletion analysis, it may be possible to identify smaller biologically active fragments of GDF15 that compete with endogenous GDF15 for its cognate receptor. Similarly, it is possible to create soluble biologically active fragments of the GDF15 receptor that compete with endogenous GDF15 receptor for available GDF. For example, "biologically active fragments" include, but are not limited to, fragments of a naturally-occurring GDF15 (or homolog) or a GDF15 receptor (or homolog) that compete with endogenous GDF15 or an endogenous GDF15 receptor, respectively, for binding to a cognate binding partner (e.g., GDF15 receptor or GDF15, respectively).

It is contemplated that antisense nucleic acids (DNA and RNA) and small interfering nucleic acids (e.g., siRNAs) can be designed and used using techniques known in the art. Exemplary siRNA inhibitors of GDF15 include siRNAs from Santa Cruz Biotech (Catalog No. sc-39799, targeting mouse GDF15; and Catalog No. sc-39798, targeting human GDF15), siRNAs from Life Technologies (Cat. Nos. AM16708, 4392420, and 1299001, targeting human GDF15; and Cat. Nos. 1320001 and 4390771, targeting mouse GDF15; and Cat. Nos. 1330001 and 4390771, targeting rat GDF15), siRNAs from Fisher Scientific (Catalog No. NC0683807, targeting human GDF15), siRNAs from Origene (Catalog No. SR306321, targeting human GDF15), siRNAs from amsbio (Catalog No. SR509800, targeting rate GDF15), siRNAs from Dharmacon (including Catalog No. D-019875-02, targeting human GDF15), siRNAs from Sigma-Aldrich (Catalog No. EHU052901, targeting human GDF15), and siRNAs described in Kim et al., 2005, Molecular Cancer Therapeutics, 4:487-493, Chang et al., 2007, Mol. Cancer Therapeutics, 6:2271-2279, and Boyle et al., 2009, J. Invest. Dermatol., 129:383-391.

IV. Formulation and Delivery of GDF15 Modulators

Pharmaceutical compositions containing GDF15 modulators, such as those disclosed herein, can be formulated into dosage forms or dosage units using standard formulation techniques. However, the pharmaceutical composition should be formulated to be compatible with its intended route of administration.

The compositions described herein can be administered to a subject via any route, including, but not limited to, intravenous (e.g., by infusion pumps), intraperitoneal, intraocular, intra-arterial, intrapulmonary, oral, inhalation, intravesicular, intramuscular, intra-tracheal, subcutaneous, intraocular, intrathecal, transdermal, transpleural, intraarterial, topical, inhalational (e.g., as mists of sprays), mucosal (such as via nasal mucosa), subcutaneous, transdermal, gastrointestinal, intraarticular, intracistemal, intraventricular, rectal (i.e., via suppository), vaginal (i.e., via pessary), intracranial, intraurethral, intrahepatic, and intratumoral. In some embodiments, the compositions are administered systemically (for example by intravenous injection). In some embodiments, the compositions are administered locally (for example by intraarterial or intraocular injection). A preferred route of administration for GDF15 modulators, such as an antibody, is via intravenous infusion.

Useful formulations can be prepared by methods well known in the pharmaceutical art. For example, see Remington's Pharmaceutical Sciences, 18th ed. (Mack Publishing Company, 1990). Formulation components suitable for parenteral administration include a sterile diluent such as bacteriostatic water for injection, physiological saline, fixed oils, polyethylene glycols, glycerine, propylene glycol or other synthetic solvents; antibacterial agents such as benzyl alcohol or methyl paraben; antioxidants such as ascorbic acid or sodium bisulfite; chelating agents such as EDTA; buffers such as acetates, citrates or phosphates; and agents for the adjustment of tonicity such as sodium chloride or dextrose. The carrier should be stable under the conditions of manufacture and storage, and should be preserved against microorganisms. In some embodiments, the composition (e.g., an antibody) is lyophilized, and then reconstituted in buffered saline, at the time of administration.

For therapeutic use, the composition (e.g., an antibody) preferably is combined with a pharmaceutically acceptable carrier. As used herein, "pharmaceutically acceptable carrier" means buffers, carriers, and excipients suitable for use in contact with the tissues of human beings and animals without excessive toxicity, irritation, allergic response, or other problem or complication, commensurate with a reasonable benefit/risk ratio. The carrier(s) should be "acceptable" in the sense of being compatible with the other ingredients of the formulations and not deleterious to the recipient. Pharmaceutically acceptable carriers include buffers, solvents, dispersion media, coatings, isotonic and absorption delaying agents, and the like, that are compatible with pharmaceutical administration. The use of such media and agents for pharmaceutically active substances is known in the art.

The pharmaceutical compositions preferably are sterile. Sterilization can be accomplished, for example, by filtration through sterile filtration membranes. Where the composition is lyophilized, filter sterilization can be conducted prior to or following lyophilization and reconstitution.

Generally, a therapeutically effective amount of active component is in the range of 0.1 mg/kg to 100 mg/kg, e.g., 1 mg/kg to 100 mg/kg, 1 mg/kg to 10 mg/kg. The amount administered will depend on variables such as the type and extent of disease or indication to be treated, the overall health of the patient, the in vivo potency of the composition (e.g., an antibody), the pharmaceutical formulation, and the route of administration. The initial dosage can be increased beyond the upper level in order to rapidly achieve the desired blood-level or tissue-level. Alternatively, the initial dosage can be smaller than the optimum, and the daily dosage may be progressively increased during the course of treatment. Human dosage can be optimized, e.g., in a conventional Phase I dose escalation study designed to run from 0.5 mg/kg to 20 mg/kg. Dosing frequency can vary, depending on factors such as route of administration, dosage amount, serum half-life of the composition (e.g., an antibody), and the disease being treated. Exemplary dosing frequencies are once per day, once per week and once every two weeks.

The optimal effective amount of the compositions can be determined empirically and will depend on the type and severity of the disease, route of administration, disease progression and health, mass and body area of the subject. Such determinations are within the skill of one in the art. Examples of dosages of GDF15 modulator molecules which can be used for methods described herein include, but are not limited to, an effective amount within the dosage range of any of about 0.01 μg/kg to about 300 mg/kg, or within about 0.1 μg/kg to about 40 mg/kg, or with about 1 μg/kg to about 20 mg/kg, or within about 1 μg/kg to about 10 mg/kg. For example, when administered subcutaneously, the composition may be administered at low microgram ranges, including for example about 0.1 μg/kg or less, about 0.05 μg/kg or less, or 0.01 μg/kg or less.

In certain embodiments, the amount of GDF15 modulators administered to a subject is about 10 μg to about 500 mg per dose, including for example any of about 10 μg to about 50 μg, about 50 μg to about 100 μg, about 100 μg to about 200 μg, about 200 μg to about 300 μg, about 300 μg to about 500 μg, about 500 μg to about 1 mg, about 1 mg to about 10 mg, about 10 mg to about 50 mg, about 50 mg to about 100 mg, about 100 mg to about 200 mg, about 200 mg to about 300 mg, about 300 mg to about 400 mg, or about 400 mg to about 500 mg per dose. In certain embodiments, a GDF15 modulator is administered at a dose from about 0.025 mg to about 4 mg, from about 0.035 mg to about 2 mg, from about 0.05 mg to about 2 mg, from about 0.1 mg to about 2 mg, from about 0.2 mg to about 1 mg, or from about 0.2 mg to about 0.8 mg of the GDF15 modulator can be administered. In one embodiment, 0.5 mg of GDF15 modulator is administered locally. In certain other embodiments, from about 0.05 mg to about 2 mg, from about 0.2 mg to about 2 mg, from about 0.05 mg to about 1.5 mg, from about 0.15 mg to about 1.5 mg, from about 0.4 mg to about 1 mg, or from about 0.5 mg to about 0.8 mg of GDF15 modulator is administered locally.

The GDF15 modulator compositions may be administered in a single daily dose, or the total daily dose may be administered in divided dosages of two, three, or four times daily. The compositions can also be administered less frequently than daily, for example, six times a week, five times a week, four times a week, three times a week, twice a week, once a week, once every two weeks, once every three weeks, once a month, once every two months, once every three months, or once every six months. The compositions may also be administered in a sustained release formulation, such as in an implant which gradually releases the composition for use over a period of time, and which allows for the composition to be administered less frequently, such as once a month, once every 2-6 months, once every year, or even a single administration. The sustained release devices (such as pellets, nanoparticles, microparticles, nanospheres, microspheres, and the like) may be administered by injection or surgical implanted in various locations in the body.

In certain embodiments of the invention, the dosing of the GDF15 modulator is titrated such that the dose is sufficient to reduce or prevent adverse effects, but yet fully or partially inhibit the activity of the GDF15.

In some aspects, the activity of GDF15 can be modulated in a target cell using antisense nucleic acids or small interfering nucleic acids. Modulation can be achieved using expression constructs known in the art, e.g., naked DNA constructs, DNA vector based constructs, and/or viral vector and/or viral based constructs to express nucleic acids encoding an anti-GDF15 siRNA or antisense molecule.

Exemplary DNA constructs and the therapeutic use of such constructs are well known to those of skill in the art (see, e.g., Chiarella et al., 2008, Recent Patents Anti-Infect. Drug Disc., 3:93-101; Gray et al., 2008, Expert Opin. Biol. Ther., 8:911-922; Melman et al., 2008, Hum. Gene Ther., 17:1165-1176). Naked DNA constructs typically include one or more therapeutic nucleic acids (e.g., GDF15 modulators) and a promoter sequence. A naked DNA construct can be a DNA vector, commonly referred to as pDNA. Naked DNA typically do not integrate into chromosomal DNA. Generally, naked DNA constructs do not require, or are not used in conjunction with, the presence of lipids, polymers, or viral proteins. Such constructs may also include one or more of the non-therapeutic components described herein.

DNA vectors are known in the art and typically are circular double stranded DNA molecules. DNA vectors usually range in size from three to five kilo-base pairs (e.g., including inserted therapeutic nucleic acids). Like naked DNA, DNA vectors can be used to deliver and express one or more therapeutic proteins in target cells. DNA vectors do not integrate into chromosomal DNA.

Generally, DNA vectors include at least one promoter sequence that allows for replication in a target cell. Uptake of a DNA vector may be facilitated by combining the DNA vector with, for example, a cationic lipid, and forming a DNA complex. Typically, viral vectors are double stranded circular DNA molecules that are derived from a virus. Viral vectors typically are larger in size than naked DNA and DNA vector constructs and have a greater capacity for the introduction of foreign (i.e., not virally encoded) genes. Like naked DNA and DNA vectors, viral vectors can be used to deliver and express one or more therapeutic nucleic acids in target cells. Unlike naked DNA and DNA vectors, certain viral vectors stably incorporate themselves into chromosomal DNA. Typically, viral vectors include at least one promoter sequence that allows for replication of one or more vector encoded nucleic acids, e.g., a therapeutic nucleic acid, in a host cell. Viral vectors may optionally include one or more non-therapeutic components described herein. Advantageously, uptake of a viral vector into a target cell does not require additional components, e.g., cationic lipids. Rather, viral vectors transfect or infect cells directly upon contact with a target cell.

The approaches described herein include the use of retroviral vectors, adenovirus-derived vectors, and/or adeno-associated viral vectors as recombinant gene delivery systems for the transfer of exogenous genes in vivo, particularly into humans. Protocols for producing recombinant retroviruses and for infecting cells in vitro or in vivo with such viruses can be found in Current Protocols in Molecular Biology, Ausubel, F. M. et al. (eds.) Greene Publishing Associates, (1989), Sections 9.10-9.14, and other standard laboratory manuals.

Viruses that are used as transduction agents of DNA vectors and viral vectors such as adenoviruses, retroviruses, and lentiviruses may be used in practicing the present invention. Illustrative retroviruses include, but are not limited to: Moloney murine leukemia virus (M-MuLV), Moloney murine sarcoma virus (MoMSV), Harvey murine sarcoma virus (HaMuSV), murine mammary tumor virus (MuMTV), gibbon ape leukemia virus (GaLV), feline leukemia virus (FLV), spumavirus, Friend murine leukemia virus, Murine Stem Cell Virus (MSCV) and Rous Sarcoma Virus (RSV)) and lentivirus. As used herein, the term "lentivirus" refers to a group (or genus) of complex retroviruses. Illustrative lentiviruses include, but are not limited to: HIV (human immunodeficiency virus; including HIV type 1, and HIV type 2); visna-maedi virus (VMV) virus; the caprine arthritis-encephalitis virus (CAEV); equine infectious anemia virus (EIAV); feline immunodeficiency virus (FIV); bovine immune deficiency virus (BIV); and simian immunodeficiency virus (SIV).

In certain embodiments, an adenovirus can be used in accordance with the methods described herein. The genome of an adenovirus can be manipulated such that it encodes and expresses a gene product of interest but is inactivated in terms of its ability to replicate in a normal lytic viral life cycle. Suitable adenoviral vectors derived from the adenovirus strain Ad type 5 dl324 or other strains of adenovirus (e.g., Ad2, Ad3, Ad7 etc.) are known to those skilled in the art. Recombinant adenoviruses can be advantageous in certain circumstances in that they are not capable of infecting nondividing cells and can be used to infect a wide variety of cell types, including epithelial cells Furthermore, the virus particle is relatively stable and amenable to purification and concentration, and as above, can be modified so as to affect the spectrum of infectivity. Additionally, introduced adenoviral DNA (and foreign DNA contained therein) is not integrated into the genome of a host cell but remains episomal, thereby avoiding potential problems that can occur as a result of insertional mutagenesis in situ where introduced DNA becomes integrated into the host genome (e.g., retroviral DNA). Moreover, the carrying capacity of the adenoviral genome for foreign DNA is large (up to 8 kilobases) relative to other gene delivery vectors.

Adeno-associated virus is a naturally occurring defective virus that requires another virus, such as an adenovirus or a herpes virus, as a helper virus for efficient replication and a productive life cycle. It is also one of the few viruses that may integrate its DNA into nondividing cells, and exhibits a high frequency of stable integration.

In various embodiments, one or more viral vectors that expresses a therapeutic transgene or transgenes encoding a GDF15 modulator is administered by direct injection to a cell, tissue, or organ of a subject, in vivo. In various other embodiments, cells are transduced in vitro or ex vivo with such a vector encapsulated in a virus, and optionally expanded ex vivo. The transduced cells are then administered to the subject. Cells suitable for transduction include, but are not limited to stem cells, progenitor cells, and differentiated cells. In certain embodiments, the transduced cells are embryonic stem cells, bone marrow stem cells, umbilical cord stem cells, placental stem cells, mesenchymal stem cells, neural stem cells, liver stem cells, pancreatic stem cells, cardiac stem cells, kidney stem cells, or hematopoietic stem cells.

In particular embodiments, host cells transduced with viral vector of the invention that expresses one or more polypeptides, are administered to a subject to treat and/or prevent an auditory disease, disorder, or condition. Other methods relating to the use of viral vectors, which may be utilized according to certain embodiments of the present invention, can be found in, e.g., Kay, 1997, CHEST, 111(6 Supp.):138S-142S; Ferry et al., 1998, HUM. GENE THER., 9:1975-81; Shiratory et al., 1999, LIVER, 19:265-74; Oka et al., 2000, CURR. OPIN. LIPIDOL., 11:179-86; Thule et al., 2000, GENE THER., 7: 1744-52; Yang, 1992, CRIT. REV. BIOTECHNOL., 12:335-56; Alt, 1995, J. HEPATOL., 23:746-58; Brody et al., 1994, ANN. N. Y. ACAD. SCI., 716:90-101; Strayer, 1999, EXPERT OPIN. INVESTIG. DRUGS, 8:2159-2172; Smith-Arica et al., 2001, CURR. CARDIOL. REP., 3:43-49; and Lee et al., 2000, NATURE, 408:483-8.

Certain embodiments of the invention provide conditional expression of a polynucleotide of interest. For example, expression is controlled by subjecting a cell, tissue, organism, etc., to a treatment or condition that causes the polynucleotide to be expressed or that causes an increase or decrease in expression of the polynucleotide encoded by the polynucleotide of interest. Illustrative examples of inducible promoters/systems include, but are not limited to, steroid-inducible promoters such as promoters for genes encoding glucocorticoid or estrogen receptors (inducible by treatment with the corresponding hormone), metallothionine promoter (inducible by treatment with various heavy metals), MX-1 promoter (inducible by interferon), the "GeneSwitch" mifepristone-regulatable system (Sirin et al., 2003, GENE, 323: 67), the cumate inducible gene switch (WO 2002/088346), tetracycline-dependent regulatory systems, etc.

Conditional expression can also be achieved by using a site specific DNA recombinase. According to certain embodiments of the invention the vector comprises at least one (typically two) site(s) for recombination mediated by a site specific recombinase. As used herein, the terms "recombinase" or "site specific recombinase" include excisive or integrative proteins, enzymes, co-factors or associated proteins that are involved in recombination reactions involving one or more recombination sites (e.g., two, three, four, five, seven, ten, twelve, fifteen, twenty, thirty, fifty, etc.), which may be wild-type proteins (see Landy, 1993, CURRENT OPINION IN BIOTECHNOLOGY, 3:699-707), or mutants, derivatives (e.g., fusion proteins containing the recombination protein sequences or fragments thereof), fragments, and variants thereof. Illustrative examples of recombinases suitable for use in particular embodiments of the present invention include, but are not limited to: Cre, Int, IHF, Xis, Flp, Fis, Hin, Gin, OC31, Cin, Tn3 resolvase, TndX, XerC, XerD, TnpX, Hjc, Gin, SpCCEl. and ParA.

The vectors may comprise one or more recombination sites for any of a wide variety of site specific recombinases. It is to be understood that the target site for a site specific recombinase is in addition to any site(s) required for integration of a vector (e.g., a retroviral vector or lentiviral vector).

In certain embodiments, vectors comprise a selection gene, also termed a selectable marker. Typical selection genes encode proteins that (a) confer resistance to antibiotics or other toxins, e.g., ampicillin, neomycin, hygromycin, methotrexate, Zeocin, Blastocidin, or tetracycline, (b) complement auxotrophic deficiencies, or (c) supply critical nutrients not available from complex media, e.g., the gene encoding D-alanine racemase for Bacilli. Any number of selection systems may be used to recover transformed cell lines. These include, but are not limited to, the herpes simplex virus thymidine kinase (Wigler et al., 1977, CELL, 11:223-232) and adenine phosphoribosyltransferase (Lowy et al., 1990, CELL, 22:817-823) genes which can be employed in tk− or aprt− cells, respectively.

All the molecular biological techniques required to generate an expression construct described herein are standard techniques that will be appreciated by one of skill in the art.

In certain embodiments, DNA delivery may occur parenterally, intravenously, intramuscularly, or even intraperitoneally as described, for example, in U.S. Pat. Nos. 5,543,158; 5,641,515; and 5,399,363 (each specifically incorporated herein by reference in its entirety). Solutions of the active compounds as free base or pharmacologically acceptable salts may be prepared in water suitably mixed with a surfactant, such as hydroxypropylcellulose. Dispersions may also be prepared in glycerol, liquid polyethylene glycols, and mixtures thereof and in oils. Under ordinary conditions of storage and use, these preparations contain a preservative to prevent the growth of microorganisms.

In certain embodiments, DNA delivery may occur by use of liposomes, nanocapsules, microparticles, microspheres, lipid particles, vesicles, optionally mixing with cell penetrating polypeptides, and the like, for the introduction of the compositions of the present invention into suitable host cells. In particular, the compositions of the present invention may be formulated for delivery either encapsulated in a lipid particle, a liposome, a vesicle, a nanosphere, a nanoparticle or the like. The formulation and use of such delivery vehicles can be carried out using known and conventional techniques.

Exemplary formulations for ex vivo DNA delivery may also include the use of various transfection agents known in the art, such as calcium phosphate, electroporation, heat shock and various liposome formulations (i.e., lipid-mediated transfection). Particular embodiments of the invention may comprise other formulations, such as those that are well known in the pharmaceutical art, and are described, for example, in REMINGTON: THE SCIENCE AND PRACTICE OF PHARMACY, 20th Edition. Baltimore, MD: Lippincott Williams & Wilkins, 2000.

In certain embodiments, GDF15 activity is inhibited by contacting a body fluid with a composition comprising a GDF15 modulator ex vivo under conditions that permit the GDF15 modulators to reduce or inhibit GDF15 activity. Suitable body fluids include those that can be returned to the individual, such as blood, plasma, or lymph. Affinity adsorption apheresis is described generally in Nilsson et al., 1988, BLOOD, 58(1):38-44; Christie et al., 1993, TRANSFUSION, 33:234-242; Richter et al., 1997, ASAIO J., 43(1):53-59; Suzuki et al., 1994, AUTOIMMUNITY, 19: 105-112; U.S. Pat. No. 5,733,254; Richter et al., 1993, METABOL. CLIN. EXP., 42:888-894; and Wallukat et al., 1996, INT'L J. CARD., 54:1910195.

Accordingly, the invention includes methods of treating one or more diseases described herein in a subject comprising treating the subject's blood extracorporeally (i.e., outside the body or ex vivo) with a composition comprising a GDF15 modulator under conditions that permit the modulator to reduce or inhibit GDF15 activity in the blood of the subject.

EXAMPLES

Example 1. GDF15 Levels in Subjects with and without Congestive Heart Failure Samples of plasma from 245 subjects were examined, and the results are summarized in FIGS. 1-6. GDF15 was assessed at a 1:50 plasma dilution with the DuoSet ELISA Development Kit (R&D Systems, #DY957) according to the manufacturer's recommendation. The inter-assay coefficient of variation (CV) was 5.6%, and the intra-assay CV was 2.9%.

Figure 2:
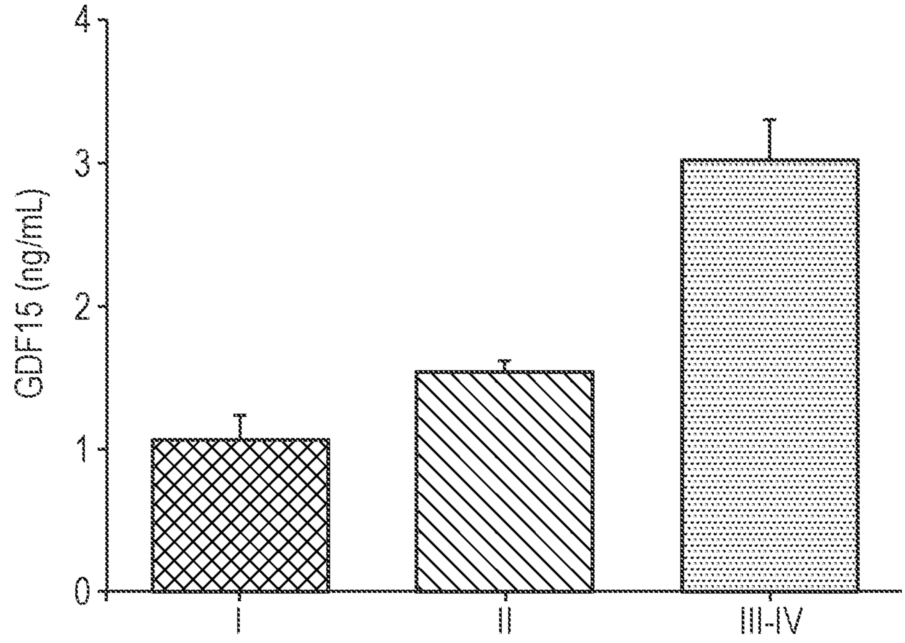
FIG. 2 is a graph illustrating the correlation between GDF15 serum levels and severity of congestive heart failure. NYHA refers to the New York Heart Association classification system (I is least severe, IV is most severe).

It was discovered that GDF15 levels were significantly higher in subjects who had been diagnosed with CHF (n=200; mean of about 1900 pg/ml GDF15 for CHF without cachexia; mean of about 3000 pg/ml GDF15 for CHF with cachexia) than in those who were not (n=45; mean of about 1000 pg/ml) (FIG. 1). GDF15 levels were significantly higher in subjects with CHF regardless of whether they presented with cachexia co-morbidity (n=33; mean of about 3000 pg/ml GDF15) or not (n=167; mean of about 1900 pg/ml GDF15) (FIG. 1). Average GDF15 levels increased with increased severity of CHF (FIG. 2).

Analysis of peak $VO_2$, a functional marker for CHF, demonstrate that the peak $VO_2$ decreased (increased severity of CHF) with increased GDF15 levels (FIGS. 3A-3C).

Figure 4:
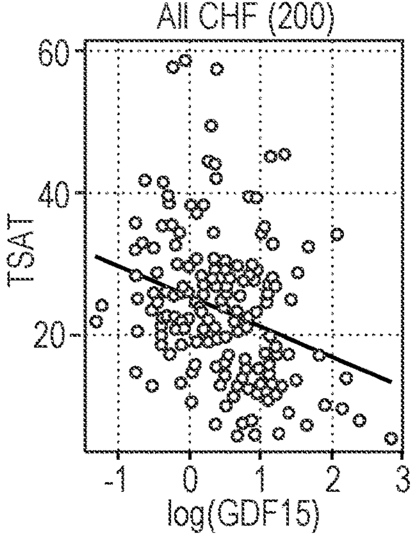
FIG. 4 is a graph illustrating the correlation between GDF15 levels and transferrin saturation (TSAT), an indicator of anemia, which is a frequent co-morbidity of cardiac failure. The accompanying table illustrates transferrin levels; iron levels; hemoglobin levels ("Hb g/dl"), erythrocyte levels and ferritin levels.

Analysis of total saturation of transferrin (TSAT), a functional marker of anemia, a frequent comorbidity of CHF, demonstrate that TSAT decreased (increased severity of anemia) with increased GDF15 levels (FIG. 4).

Analysis of creatinine and urea levels, which are markers of renal function, another frequent comorbidity of CHF, demonstrate that creatinine levels are increased (increased severity of renal impairment) in subjects with CHF (both with and without cachexia) together with increased GDF15 levels (FIGS. 5A and 5B). Urea levels also increased (increased severity of renal impairment) with increased GDF15 levels in subjects with CHF, in the absence of cachexia (FIG. 5C).

Figures 6A, 6B, 6C, 6D:
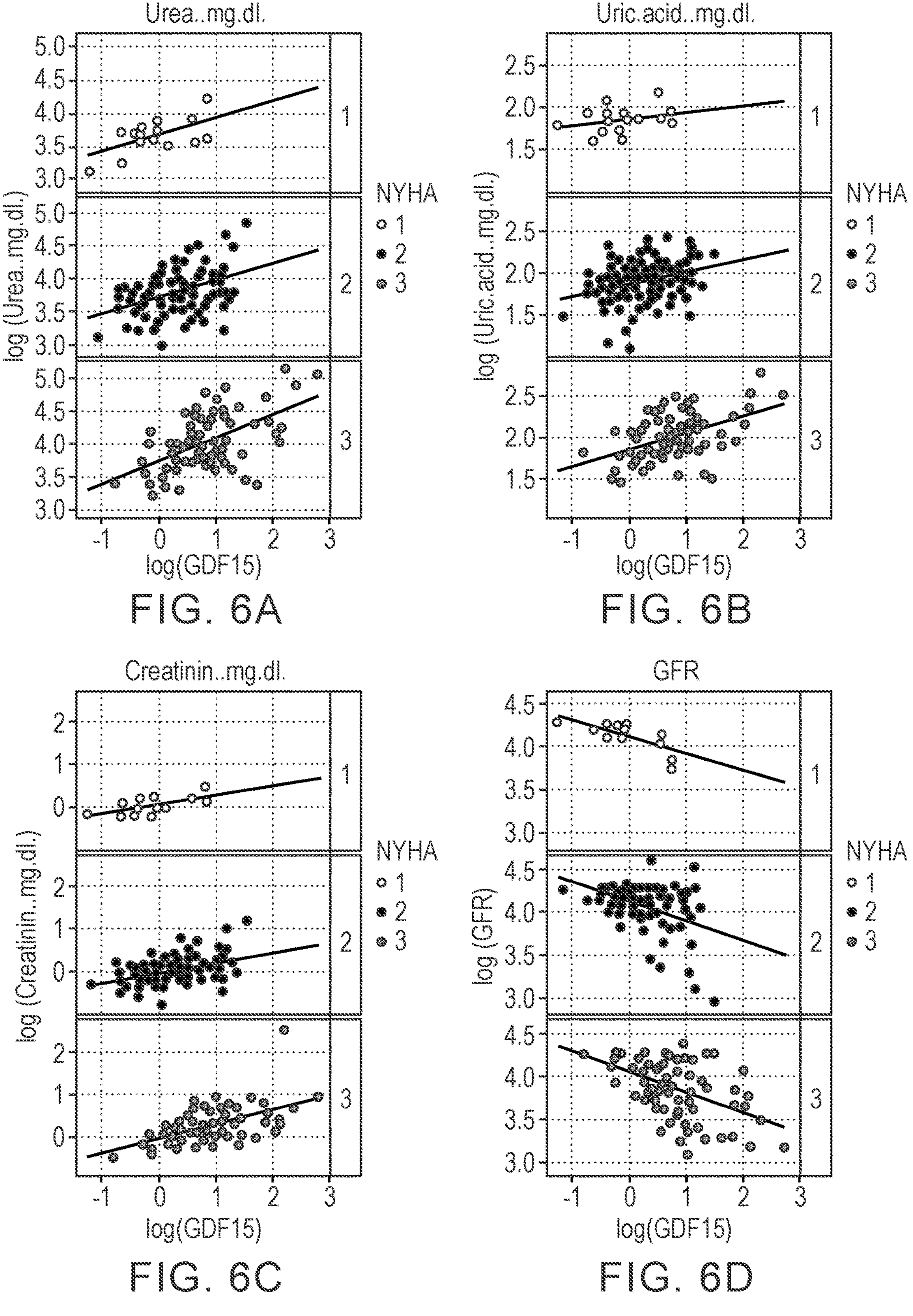
FIGS. 6A-6D are graphs illustrating the correlation between GDF15 levels and various markers of kidney disease, a frequent co-morbidity of CHF, across subjects with CHF stages I-III (Stage IV was not included due to low number of subjects), including urea (FIG. 6A), where urea level increased with GDF15 level; uric acid (FIG. 6B), where uric acid level increased with GDF15 level; creatinine (FIG. 6C), where creatinine level increased with GDF15 level; and glomerular filtration rate (GFR) (FIG. 6D), where GFR decreased with GDF15 level.

Analysis of renal function markers in 200 subjects with CHF demonstrate that levels of urea, uric acid and creatinine all increased (increased renal impairment) with increased GDF15 levels (FIGS. 6A, 6B and 6C), while glomerular filtration rate (GFR), a measure of kidney function, decreased with increased GDF15 levels (FIG. 6D).

Example 2. Treatment of Cardiac Hypotrophy in an HT-1080 Xenograft Tumor Model This Example demonstrates the treatment of cardiac hypotrophy (as indicated by heart weight loss) with an anti-GDF15 antibody 01G06 in an HT-1080 fibrosarcoma xenograft model.

HT-1080 cells were grown in culture at 37° C. in an atmosphere containing 5% $CO_2$, using Eagle's Minimum Essential Medium (ATCC, Catalog No. 30-2003) containing 10% FBS. Cells were inoculated subcutaneously into the flank of 8-week old female ICR SCID mice with $5\times10^6$ cells per mouse in 50% matrigel. Body weight was measured daily. When body weight reached 80%, the mice were randomized into two groups of five mice each. Each group received one of the following treatments: murine IgG control ("mIgG"), or 01G06 dosed at 2 mg/kg on day 1 and day 7, via intra-peritoneal injection. Treatment with antibody 01G06 resulted in body weight increase to initial weight or 100% ($p<0.001$) (FIG. 7A).

Figure 7A:
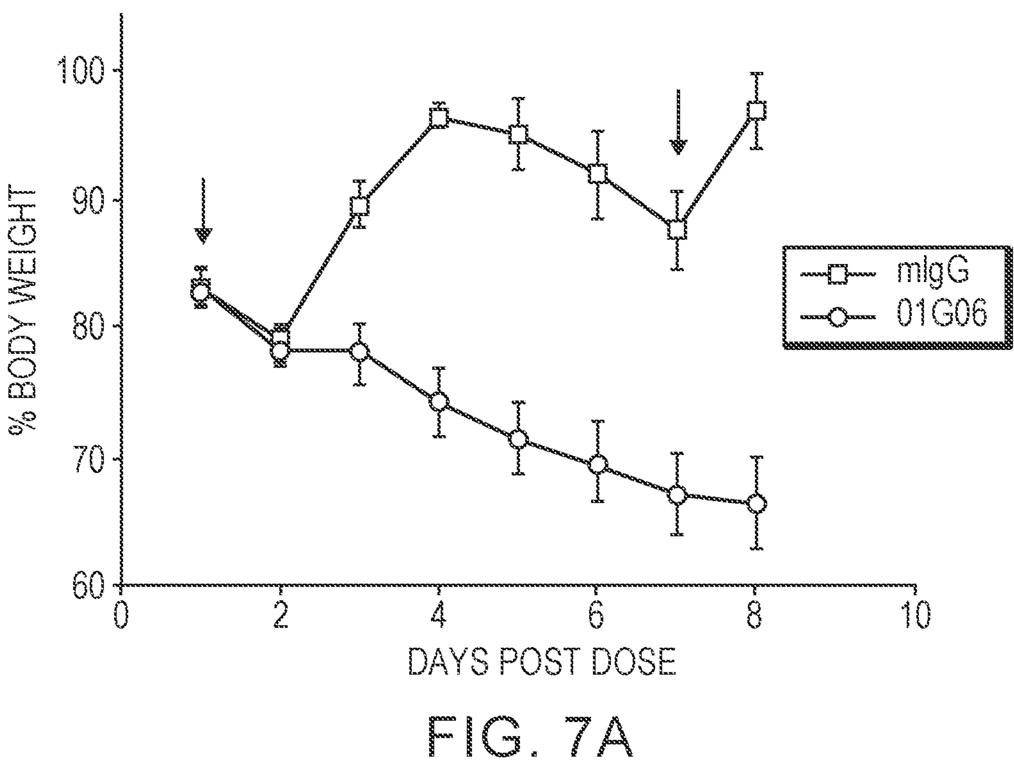
FIGS. 7A-7B are graphs summarizing results from an experiment to demonstrate the activity of anti-GDF15 antibody 01G06 (■), dosed at 2 mg/kg, in immune-incompetent mice (ICR-SCID) bearing an HT-1080 fibrosarcoma tumor xenograft model. Treatment with antibody 01G06 reversed body weight loss (FIG. 7A), induced a gain of organ mass (liver, heart, spleen and kidney) and induced a gain of tissue mass (gonadal and gastrocnemius) (FIG. 7B), compared to the negative control (murine IgG (●) and baseline (day 1). Vertical arrows indicate days where antibody was administered to test animals via intra-peritoneal injection (FIG. 7A).
Figure 7B:
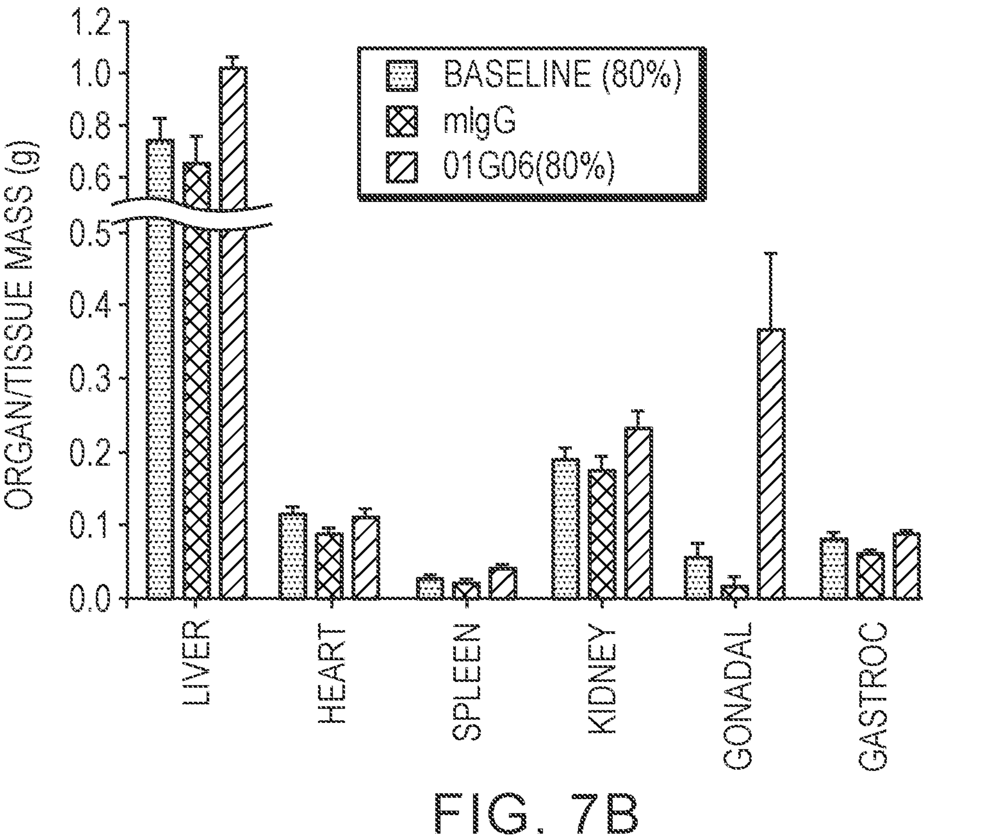

The data in FIGS. 7A-B indicate that administration of the anti-GDF15 antibody can reverse heart weight loss in an HT-1080 fibrosarcoma xenograft model.

In this experiment, a group of five mice were sacrificed at the time of dosing (baseline or 80% body weight loss, without treatment) and at the end of study (seven days post dose, either mIgG or 01G06). Liver, heart, spleen, kidney, gonadal fat and the gastrocnemius muscles were removed surgically and weighed. As shown in FIG. 7B, a significant loss in liver, heart, spleen, kidney, gonadal fat and gastrocnemius muscle mass was observed seven days post dose with mIgG, but not in the group treated with antibody 01G06.

These results indicate that administration of the anti-GDF15 antibody reserves the loss of key organ mass, such as heart, loss of muscle mass, loss of fat and involuntary weight loss in an HT-1080 xenograft tumor model.

Figure 8:
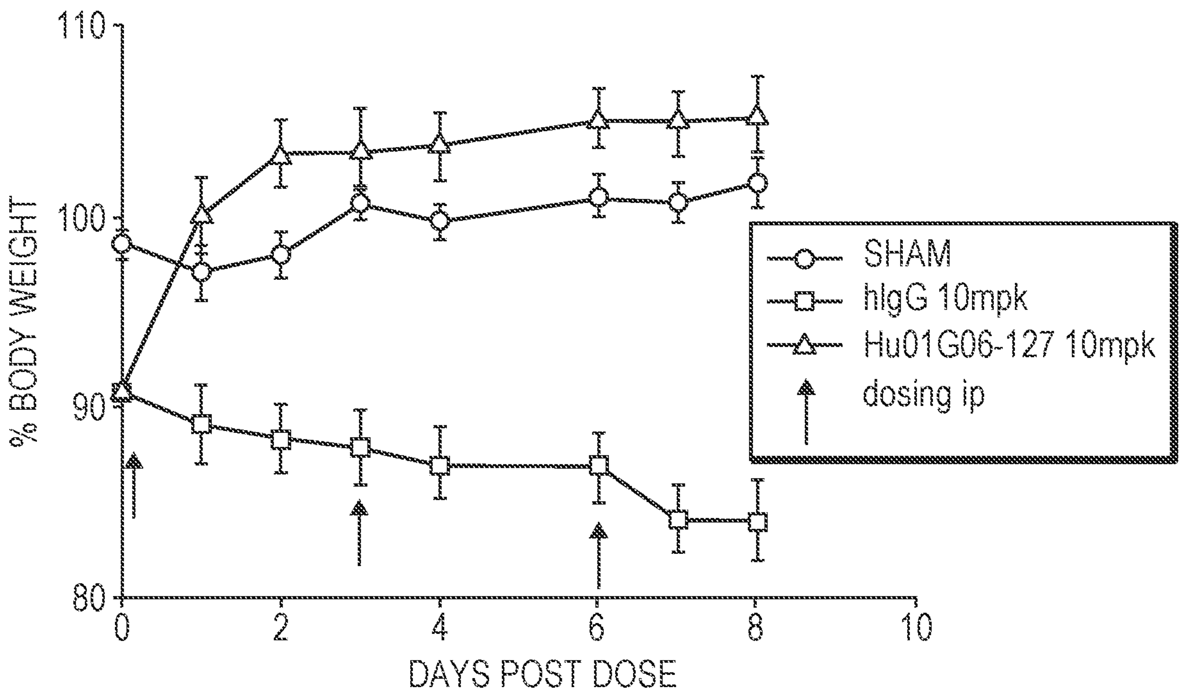
FIG. 8 is a graph illustrating the effects of systemic administration of a monoclonal antibody that binds to and inhibits human GDF15 (Hu01G06-127) on body weight in cachexic mice bearing human tumor xenografts (▲) compared to similar mice following administration of human IgG (■) and compared to sham mice (no tumor) (●).

In a similar experiment, the effects of systemic administration of a monoclonal antibody that binds to and inhibits human GDF15 (Hu01G06-127) on body weight in cachexic mice bearing human tumor xenografts were compared to similar animals receiving human IgG or sham mice (i.e., no tumor). Administration of the anti-GDF15 antibody resulted in retention or increase in body weight, compared to the mice without tumors, while mice that were injected with human IgG exhibited significant loss in body weight (FIG. 8).

Example 3. In Vivo Model of Pressure-Induced Cardiac Hypertrophy

A reproducible transverse aortic constriction of 65-70% is made in mice, as described in Rockman et al., 1991, PROC. NATL ACAD. SCI., 88:8277-8291. The animals are extubated and allowed to recover, and blood pressure in the left and right carotids is measured. Animals then are dosed with either an anti-GDF15 antibody or control. After seven days, heart size and weight are assessed for the existence and/or extent of cardiac hypertrophy.

Example 4: In Vivo Model of Heart Failure Due to Chronic Volume Overload

An aortocaval shunt is implanted in mice, as described in Scheuermann-Freestone et al., 2001, EUR. J. HEART FAILURE, 3:535-543. Animals are dosed with either an anti-GDF15 antibody or control. After thirty days, animals are assessed for mortality, development of myocardial hypertrophy, hemodynamic parameters, and expression levels of BNP-mRNA.

Example 5: Treatment of Subjects Previously Treated with Other Cardiac Interventions Subjects exhibiting cardiac hypotrophy, who have previously been treated with known cardiac interventions, but who exhibit at least one characteristic of congestive heart failure, are dosed with anti-GDF15 antibody. Treatment with anti-GDF15 antibody lasts for a duration of three months, during which heart size, peak $VO_2$, troponin levels and BNP levels are monitored at regular intervals.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and the range of equivalency of the claims are intended to be embraced therein.

The invention claimed is:

1. A method of treating cardiac hypotrophy in a subject in need thereof, the method comprising administering to the subject an effective amount of an anti-GDF15 antibody selected from the group consisting of a) an antibody comprising the heavy chain sequence of SEQ ID NO:47 or 49 and the light chain sequence of SEQ ID NO:30;

b) an antibody comprising the heavy chain sequence of SEQ ID NO:41, 42, 43, 44, 45, 46, 48, or 49 and the light chain sequence of SEQ ID NO:29;

c) an antibody comprising the heavy chain sequence of SEQ ID NO:41, 42, 43, 44, or 45 and the light chain sequence of SEQ ID NO:28;

d) an antibody comprising the heavy chain sequence of SEQ ID NO:39, 40, 41, 42, 43, 44, or 45 and the light chain sequence of SEQ ID NO:27;

e) an antibody comprising the heavy chain sequence of SEQ ID NO:38 and the light chain sequence of SEQ ID NO:26;

f) an antibody comprising the heavy chain sequence of SEQ ID NO:37 and the light chain sequence of SEQ ID NO:25;

g) an antibody comprising a heavy chain $CDR_{H1}$ sequence of SEQ ID NO:1, a heavy chain $CDR_{H2}$ sequence of SEQ ID NO:7, and a heavy chain $CDR_{H3}$ sequence of SEQ ID NO:13; and
a light chain $CDR_{L1}$ sequence of SEQ ID NO:16, a light chain $CDR_{L2}$ sequence of SEQ ID NO:18, and a light chain $CDR_{L3}$ sequence of SEQ ID NO:22;

h) an antibody comprising a heavy chain $CDR_{H1}$ sequence of SEQ ID NO:1, a heavy chain $CDR_{H2}$ sequence of SEQ ID NO:9, and a heavy chain $CDR_{H3}$ sequence of SEQ ID NO:13; and
a light chain $CDR_{L1}$ sequence of SEQ ID NO:16, a light chain $CDR_{L2}$ sequence of SEQ ID NO:18, and a light chain $CDR_{L3}$ sequence of SEQ ID NO:22;

i) an antibody comprising a heavy chain $CDR_{H1}$ sequence of SEQ ID NO:1, a heavy chain $CDR_{H2}$ sequence of SEQ ID NO:4, and a heavy chain $CDR_{H3}$ sequence of SEQ ID NO:13; and
a light chain $CDR_{L1}$ sequence of SEQ ID NO:16, a light chain $CDR_{L2}$ sequence of SEQ ID NO:18, and a light chain $CDR_{L3}$ sequence of SEQ ID NO:21;

j) an antibody comprising a heavy chain $CDR_{H1}$ sequence of SEQ ID NO:1, a heavy chain $CDR_{H2}$ sequence of SEQ ID NO:5, and a heavy chain $CDR_{H3}$ sequence of SEQ ID NO:13; and
a light chain $CDR_{L1}$ sequence of SEQ ID NO:16, a light chain $CDR_{L2}$ sequence of SEQ ID NO:18, and a light chain $CDR_{L3}$ sequence of SEQ ID NO:21;

k) an antibody comprising a heavy chain $CDR_{H1}$ sequence of SEQ ID NO:1, a heavy chain $CDR_{H2}$ sequence of SEQ ID NO:6, and a heavy chain $CDR_{H3}$ sequence of SEQ ID NO:13; and
a light chain $CDR_{L1}$ sequence of SEQ ID NO:16, a light chain $CDR_{L2}$ sequence of SEQ ID NO:18, and a light chain $CDR_{L3}$ sequence of SEQ ID NO:21;

l. an antibody comprising a heavy chain $CDR_{H1}$ sequence of SEQ ID NO:1, a heavy chain $CDR_{H2}$ sequence of SEQ ID NO:8, and a heavy chain $CDR_{H3}$ sequence of SEQ ID NO:13; and
a light chain $CDR_{L1}$ sequence of SEQ ID NO:16, a light chain $CDR_{L2}$ sequence of SEQ ID NO:18, and a light chain $CDR_{L3}$ sequence of SEQ ID NO:21; and m) an antibody comprising a heavy chain $CDR_{H1}$ sequence of SEQ ID NO:1, a heavy chain $CDR_{H2}$ sequence of SEQ ID NO:9, and a heavy chain $CDR_{H3}$ sequence of SEQ ID NO:13; and
a light chain $CDR_{L1}$ sequence of SEQ ID NO:16, a light chain $CDR_{L2}$ sequence of SEQ ID NO:18, and a light chain $CDR_{L3}$ sequence of SEQ ID NO:21, thereby reducing or inhibiting GDF15 activity in the subject.

2. The method of claim 1, wherein the antibody is humanized or human.

3. The method of claim 1, wherein the anti-GDF15 antibody comprises the heavy chain sequence of SEQ ID NO:47 and the light chain sequence of SEQ ID NO:30.

4. The method of claim 1, wherein the anti-GDF15 antibody comprises a heavy chain $CDR_{H1}$ sequence of SEQ ID NO:1, a heavy chain $CDR_{H2}$ sequence of SEQ ID NO:7, and a heavy chain $CDR_{H3}$ sequence of SEQ ID NO:13; and a light chain $CDR_{L1}$ sequence of SEQ ID NO:16, a light chain $CDR_{L2}$ sequence of SEQ ID NO:18, and a light chain $CDR_{L3}$ sequence of SEQ ID NO:22.

5. The method of claim 1, wherein the anti-GDF15 antibody comprises the heavy chain sequence of SEQ ID NO:48 and the light chain sequence of SEQ ID NO:29.

6. The method of claim 1, wherein the anti-GDF15 antibody comprises a heavy chain $CDR_{H1}$ sequence of SEQ ID NO:1, a heavy chain $CDR_{H2}$ sequence of SEQ ID NO:8, and a heavy chain $CDR_{H3}$ sequence of SEQ ID NO:13; and a light chain $CDR_{L1}$ sequence of SEQ ID NO:16, a light chain $CDR_{L2}$ sequence of SEQ ID NO:18, and a light chain $CDR_{L3}$ sequence of SEQ ID NO:21.

* * * * *